(12) United States Patent
Tambourgi et al.

(10) Patent No.: US 10,081,660 B2
(45) Date of Patent: Sep. 25, 2018

(54) POLYNUCLEOTIDE, POLYPEPTIDE WITH IMMUNOSUPPRESSIVE ACTIVITY, EXPRESSION CASSETTE, EXPRESSION VECTOR, HOST CELL, PHARMACEUTICAL COMPOSITION, METHODS FOR PRODUCING A POLYPEPTIDE WITH IMMUNOSUPPRESSIVE ACTIVITY AND FOR PREVENTING OR TREATING CONDITIONS THAT REQUIRE IMMUNOSUPPRESSION, AND USE OF A POLYPEPTIDE

(71) Applicant: FUNDAÇÃO BUTANTAN, São Paulo (BR)

(72) Inventors: Denise V. Tambourgi, São Paulo (BR); Giselle Pidde Queiroz, São Paulo (BR); Osvaldo Augusto Brazil Esteves Sant'Anna, São Paulo (BR); Fábio Carlos Magnoli, São Paulo (BR); Ogari de Castro Pacheco, Itapira (BR)

(73) Assignee: FUNDAÇÃO BUTANTAN, São Paulo (BR)

( * ) Notice: Subject to any disclaimer, the term of this patent is extended or adjusted under 35 U.S.C. 154(b) by 0 days.

(21) Appl. No.: 15/031,936

(22) PCT Filed: Oct. 24, 2014

(86) PCT No.: PCT/BR2014/000387
§ 371 (c)(1),
(2) Date: Apr. 25, 2016

(87) PCT Pub. No.: WO2015/058275
PCT Pub. Date: Apr. 30, 2015

(65) Prior Publication Data
US 2016/0311869 A1    Oct. 27, 2016

(30) Foreign Application Priority Data
Oct. 25, 2013  (BR) .................... BR1020130276480

(51) Int. Cl.
| C07K 14/46 | (2006.01) |
| A61K 38/16 | (2006.01) |
| A61K 39/38 | (2006.01) |
| A61K 39/00 | (2006.01) |
| C07K 14/47 | (2006.01) |
| A61K 38/00 | (2006.01) |

(52) U.S. Cl.
CPC ............ C07K 14/46 (2013.01); A61K 39/001 (2013.01); A61K 39/38 (2013.01); C07K 14/4713 (2013.01); A61K 38/00 (2013.01)

(58) Field of Classification Search
CPC ...... A61K 39/38; A61K 38/00; A61K 39/001; C07K 14/46; C07K 14/4713
See application file for complete search history.

(56) References Cited

U.S. PATENT DOCUMENTS 6,809,179 B1 * 10/2004 Konopitzky ....... C07K 14/4711
424/185.1
2011/0319345 A1 * 12/2011 Markland, Jr. .... A61K 38/1703
514/21.2

FOREIGN PATENT DOCUMENTS

| BR | P10502080 | 1/2007 |
| CN | 101319002 A * 12/2008 ............... C07K 7/08 |
| WO | 2008109972 A1 | 9/2008 |

OTHER PUBLICATIONS

Zhou et al, Molecular cloning and expression of catrocollastatin, a snake-venom protein from Crotalus atrox (western diamondback rattlesnake) which inhibits platelet adhesion to collagen, Biochem. J., 1995, 307, pp. 411-417.*
Water, from http://www.biology-online.org/dictionary/Water, pp. 1-3, accessed Apr. 24, 2014.*
Glutamine, from http://www.webmd.com/vitamins-supplements/ingredientmono-878-glutamine.aspx?activeingredientid=878&print=true&print=true&print=true, pp. 1-3, accessed Aug. 29, 2017.*
Machine translation of CN 101319002 A, pp. 1-8, accessed Aug. 29, 2017.*
Sf-900 Medium, from https://www.thermofisher.com/order/catalog/product/10967032, pp. 1-4, accessed Aug. 29, 2017.*
Zhou et al, The Hemorrhagin Catrocollastatin Inhibits Collagen-Induced Platelet Aggregation by Binding to Collagen via Its Disintegrin-like Domain, Biochemical and Biophysical Research Communications, 1996, 219, pp. 720-726.*
Quinlan et al, Albumin: Biochemical Properties and Therapeutic Potential, Hepatology, 2005, 41, pp. 1211-1219.*
Yampolsky et al, The Exchangeability of Amino Acids in Proteins, Genetics, 2005, 170, pp. 1459-1472.*
International Search Report for PCT/BR2014/000387, dated Mar. 27, 2015.
Sanchez et al., "The complete amino acid sequence of the haemorrhagic factor LHFII, a metalloproteinase isolated from the venom of the bushmaster snake (*Lachesis muta muta*)," Federation of European Biochemical Societies, Apr. 1991, vol. 282, No. 1, pp. 178-182.
Junqueira-de-Azevedo et al., "*Lachesis muta* (Viperidae) cDNAs Reveal Diverging Pit Viper Molecules and Scaffolds Typical of Cobra (*Elapidae*) Venoms: Implications for Snake Toxin Repertoire Evolution," Genetics 173, 877-89, 2006.

* cited by examiner

Primary Examiner — Julie Ha
Assistant Examiner — Li N Komatsu
(74) Attorney, Agent, or Firm — Banner & Witcoff, Ltd.

(57) ABSTRACT

This invention refers to polynucleotides and non-hemorrhagic and non-immunogenic polypeptides of selective immunosuppressive activity on production of antibodies to antigens of different natures. The polypeptides described herein are useful for preparing pharmaceutical compositions for prevention or treatment of conditions that require immunos

Figure 1:
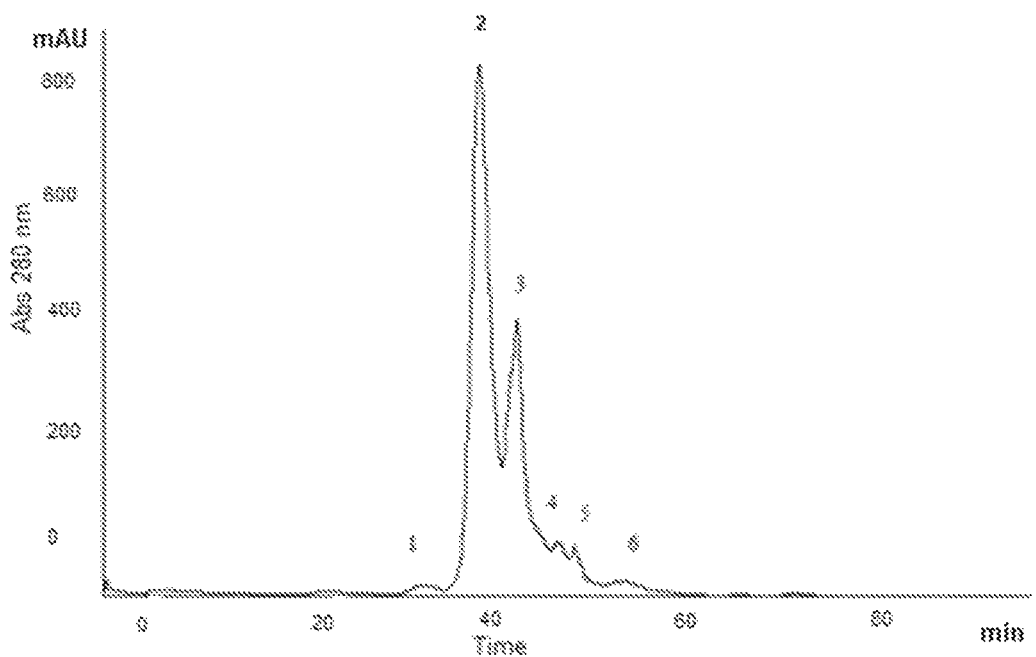

```
         ....|....|  ....|....|  ....|....|  ....|....|  ....|....|
             10          20          30          40          50
         FSQKYIELVY VADHQMFTKY NGNLNTIRTR VHEIVNIING FYRSLNILIS

....|....|  ....|....|  ....|....|  ....|....|  ....|....|
             60          70          80          90          100
         LIDLEIWSNQ DLINVQSAAN DTLKIFGENR ERVLLNRISH DNAQLLTAID

....|....|  ....|....|  ....|....|  ....|....|  ....|....|
             110         120         130         140         150
         LADNTIGIAY TGGMCYPKNS VGIVQDHSEN LLTAVIMAH ELGHNLGMKH

....|....|  ....|....|  ....|....|  ....|....|  ....|....|
             160         170         180         190         200
         DENHCHCSAS FCIMPPSISE GPSYEFSDCS KDYYQMFLTK NKPQCILNKP
```

FIGURE 4

```
XhoI
CTCGAG    ───▶ Primer sense ──────▶
  1       TTC TCA CAG AAA TAC ATT GAA CTT GTT GTA GTT GCA GAT CAC GGA    45
  1        F   S   Q   K   Y   I   E   L   V   V   V   A   D   H   G    15

46       ATG TTC ACG AAA TAC AAT GGC AAT TTA AAT ACT ATA AGA ACA CGG    90
 16        M   F   T   K   Y   N   G   N   L   N   T   I   R   T   R    30

91       GTA CAT GAA ATT GTC AAC ACT CTA AAT GGG TTT TAC AGA TCT TTG   135
 31        V   H   E   I   V   N   T   L   N   G   F   Y   R   S   L    45

136       AAT ATT CAT ATC TCA CTG ACT GAC CTA GAA ATT TGG TCC AAC CAA   180
 46        N   I   H   I   S   L   T   D   L   E   I   W   S   N   Q    60

181       GAT TTG ATC AAC GTG CAG TCA GCA GCG GCT GAT ACT TTG AAA ACA   225
 61        D   L   I   N   V   Q   S   A   A   A   D   T   L   K   T    75

226       TTT GGA GAG TGG AGA GAG AGA GTC TTG CTG AAT CGC ATA AGT CAT   270
 76        F   G   E   W   R   E   R   V   L   L   N   R   I   S   H    90

271       GAT AAT GCT CAG TTA CTC ACG GCC ATT GAC CTT GCT GAT AAT ACT   315
 91        D   N   A   Q   L   L   T   A   I   D   L   A   D   N   T   105

316       ATA GGA ATA GCT TAC ACA GGC GGC ATG TGC TAC CCG AAG AAT TCT   360
106        I   G   I   A   Y   T   G   G   M   C   Y   P   K   N   S   120

361       GTA GGA ATT GTT CAG GAT CAT AGT CCA AAA ACT CTT TTG ATT GCA   405
121        V   G   I   V   Q   D   H   S   P   K   T   L   L   I   A   135

406       GTT ACA ATG GCC CAT GAG CTG GGT CAT AAT CTG GGC ATG AAG CAT   450
136        V   T   M   A   H   E   L   G   H   N   L   G   M   K   H   150

451       GAT GAA AAT CAT TGT CAT TGC AGT GCT TCC TTC TGC ATT ATG CCT   495
151        D   E   N   H   C   H   C   S   A   S   F   C   I   M   P   165

496       CCC AGT TTA AGT GAA GGA CCT TCC TAT GAG TTC AGC GAT TGT AGT   540
166        P   S   L   S   E   G   P   S   Y   E   F   S   D   C   S   180

541       AAG GAT TAT TAT GAG ATG TTT CTT ACT AAG CGA AAG CCA CAA TGC   585
181        K   D   Y   Y   E   M   F   L   T   K   R   K   P   Q   C   195

NcoI
          ◀── Primer Anti-sense ◀── CCATGG

586       ATC CTG AAC AAG CCA    600
196        I   L   N   K   P     200
```

FIGURE 7

FIGURE 8

POLYNUCLEOTIDE, POLYPEPTIDE WITH IMMUNOSUPPRESSIVE ACTIVITY, EXPRESSION CASSETTE, EXPRESSION VECTOR, HOST CELL, PHARMACEUTICAL COMPOSITION, METHODS FOR PRODUCING A POLYPEPTIDE WITH IMMUNOSUPPRESSIVE ACTIVITY AND FOR PREVENTING OR TREATING CONDITIONS THAT REQUIRE IMMUNOSUPPRESSION, AND USE OF A POLYPEPTIDE

This application is a U.S. national stage application of PCT/BR2014/000387 filed on Oct. 24, 2014, which claims priority to Brazilian application 1020130276480 filed on Oct. 25, 2013.

This application incorporates by reference the contents of a 34 kb text file created on Apr. 3, 2018 and named "15031936substitutesequencelisting.txt," which is the sequence listing for this application.

This invention concerns to the field of immunology and biotechnology. This invention refers, particularly, to polypeptides useful in prevention and treatment of conditions that require immunosuppression, preferably inflammatory, autoimmune, allergic, and infectious diseases and rejection to transplanted organs.

STATE OF THE ART

The immune system keeps the organism's physical integrity and homeostasis, being essential for the defense against foreign agents, exogenous or endogenous, such as pathogens and neoplastic, senescent, and immunologically auto-reactive cells, and having fundamental importance for the individual's survival. Failure in one or more immune system elements can cause serious or even fatal disorders.

The immune response can be divided, for didactic purposes, in innate and acquired immunity, which are genetically independent, have their own characteristics, are activated by different stimuli, but functionally integrated. The innate immune response corresponds to a set of elements that quickly respond to molecular patterns recognized as foreign. It is responsible for the initial immune response; it involves the complement system, natural killer cells, phagocytic mononuclear system cells, and physicochemical barriers.

The acquired immune response is specific to the foreign agent and is distinguished by the establishment of memory. T and B cells are responsible for this response. They carry receptors with variable regions for specific recognition capable of discriminating different molecules and trigger a complex response, involving antibodies production (humoral immunity) and/or effector T lymphocytes activation (cellular immunity).

Both innate and acquired immune responses are components of an integrated defense system of the organism, in which many cells and molecules cooperate. On initial phases, there is a prevalence of the innate immune response which, in its turn, stimulates and influences the nature of acquired responses. On the other hand, acquired responses use many innate immunity effector mechanisms that, usually, expand its defense mechanisms.

The immune system regulation is driven by the interaction among multiple control mechanisms, since its repertoire is complex and diverse. Immunoregulators, such as cytokine, suppressive cells and effector cells, set the balance between the immune response activation and suppression. When immunosuppression mechanisms are inhibited, the organism loses its ability to distinguish between self and non-self and, thus, autoimmune responses arise, besides exacerbated immune responses, leading to irreversible cell damage. On the other hand, deficiency or anergy of cells and mechanisms responsible for the regulation of the immune system activation leads to immunosuppression, increasing the organism's vulnerability, for instance, to infections and neoplasms development.

The immune system suppression could be originated naturally, as in congenital and acquired immunodeficiencies, or induced by immunosuppressive compounds.

Immunosuppression induction is used for the treatment of inflammatory, autoimmune, allergic, and infectious diseases, to reduce their clinical signs, as well as in transplant patients, with the purpose of prevention and treatment of transplanted organ rejection. These substances might be biological or synthetic agents.

The current immunosuppressive therapeutic arsenal includes small molecules (target of rapamycin inhibitors, antimetabolic agents, and calcineurin inhibitors), recombinant proteins, glucocorticoids, lymphocyte depletion or non-depletion inducing proteins (monoclonal antibodies) and intravenous immunoglobulin.

The immunosuppressants inhibit, either directly or indirectly, active immunocompetent cells and might act on the immune system in multiple ways, e.g., interfering on cell surface receptors that participate on antigen recognition, blocking the expression of cytokines or their receptors, destroying or inhibiting the proliferative activity of cells responsible for unwanted immune reaction.

The main disadvantage of using immunosuppressants is the nonspecific action on immune response reduction, increasing the organism's vulnerability to opportunist infections and neoplasms development. Besides, other adverse effects of current immunosuppressives include chronic nephrotoxicity, hepatotoxicity, hypertension, dyslipidemia, and others.

In regards to their adverse effects, it is worth mentioning some immunosuppressant agents for their use and scope. Glucocorticoids suppress the immune response on its initial phase and present severe adverse effects, such as Cushing's syndrome, gastrointestinal ulcers, delayed wound healing, muscles and skin atrophy, and diabetogenic effects. Therefore, the use of glucocorticoids requires periodic treatment interruptions. Cytostatics, due to their antiproliferative activities, lead to severe adverse effects such as haematopoiesis alterations, gastrointestinal symptoms, and loss of appetite, and should not be used for long periods. Cyclosporin A diminishes both humoral and cellular immune response, especially by inhibiting the secretion of interleukin-1 (IL-1), by the monocytes, and IL-2, by T helper (Th) lymphocytes at the early stages of immune response. An important adverse effect of this compound is the dose-dependent kidney deterioration. Other adverse effects include hepatic disturbances, cardiotoxicity, tremor, hirsutism, gum hypertrophy, and edema. Monoclonal antibodies induce adverse effects such as fever, dyspnea, and gastrointestinal symptoms. Furthermore, in cases of non-human antibodies, such as chimeric or murine, there might be loss of response efficiency, due to formation of human anti-murine/chimeric antibody.

In the effort to minimize adverse effects, the scope of the immunosuppressant action has been controlled by the combination of different suppressive agents.

New compounds with more selective suppressive effect and, thus, reduced adverse effects, have been investigated.

However, it is still possible to state that the prevention or treatment of conditions benefiting from immunosuppressive effects, such as inflammatory, autoimmune, allergic, and infectious diseases and rejection to transplanted organs, is usually difficult and disappointing.

It is known that snake venom contain a diverse range of substances with different biochemical and pharmacological properties, and more than 90% of dry weight of the venom correspond to proteins, including enzymes, toxins, and small peptides. Other substances, such as carbohydrates, lipids, metals, biogenic amines, nucleotides, and free amino acids, represent its non-protein portion.

Stephano et al. (Brazilian Patent Application BRPI0502080-8, 2005) observed the reduced production of neutralizing antibodies for venoms of snakes of the genus *Lachesis* in equines, suggesting that some factor within this venom interfered on the efficient immune response in these animals. Through molecular exclusion chromatography, the whole *Lachesis muta* venom was split in six different fractions, and two of them presented effect on antibody production (designated as fractions IV and V).

The patent application BRPI0502080-8 describes that removing these fractions of the venom and subsequently immunizing the horses, allowed the effective achievement of neutralizing antibodies for therapeutic use, obtaining anti-lachetic equine serum with the venom neutralization efficiency increased eight times.

Under this context, this invention describes polypeptides with immunosuppressive activity, selective and signal dependent, inhibiting the production of antibodies with small dosage and no adverse effects usually observed for the immunosuppressants already known in the state of the art. These and other advantages of this invention, as well as additional inventive characteristics related to the same inventive concept, will be evidenced in the description of the invention provided in this document.

Invention Summary

In one aspect, this invention provides a polynucleotide that encodes a polypeptide with immunosuppressive activity, selected from the group consisting of: (a) polynucleotides comprising a sequence of nucleotides as presented on SEQ ID NO: 1; (b) nucleic acids that hybridize under stringent conditions with the nucleic acid from SEQ ID NO: 1: (c) polynucleotides encoding a polypeptide which is at least 70% identical to the amino acid sequence of SEQ ID NO: 2: (d) polynucleotides encoding a polypeptide which is at least 70% identical to the amino acid sequence of SEQ ID NO: 3: (e) polynucleotides encoding a polypeptide which is at least 70% identical to the amino acid sequence of SEQ ID NOs: 4-15: and (f) degenerated nucleotide sequences (a)-(e).

In one embodiment, the polynucleotide is a cDNA, genomic DNA, synthetic DNA or RNA.

In another aspect, the invention provides an expression cassette comprising a polynucleotide as defined above operationally linked to a transcription promoter and terminator.

In another aspect, an expression vector is provided comprising a polynucleotide or an expression cassette as described above.

In another aspect, the invention provides a host cell comprising an expression cassette or an expression vector comprising said polynucleotide.

In another aspect, it is provided a polypeptide having immunosuppressive activity, selected from the group consisting of: (a) a polypeptide comprising the amino acid sequence as shown in SEQ ID NO: 2; (b) a polypeptide comprising the amino acid sequence as shown in SEQ ID NO: 3; (c) a polypeptide comprising any amino acid sequence shown in SEQ ID NOs: 4-15; (d) a polypeptide comprising an amino acid sequence having at least 70% identity with the sequences of any one of SEQ ID NOs: 2-15.

In an embodiment, the polypeptide is useful for prevention or treatment of conditions requiring immunosuppression. In a further embodiment, the conditions requiring immunosuppression are selected from the group consisting of inflammatory, autoimmune, allergic, and infectious diseases, and rejection of transplanted organs.

In another aspect, the invention provides a pharmaceutical composition comprising a polypeptide of the present invention, or pharmaceutically acceptable salts thereof, and a pharmaceutically acceptable carrier or excipient. In one embodiment, the composition is combined with an additional therapeutic agent.

In a further aspect, it is provided the use of an immunosuppressive polypeptide, or pharmaceutically acceptable salts thereof, in the manufacture of a medicament for the prevention or treatment of conditions requiring immunosuppression. In one embodiment, the conditions requiring immunosuppression are selected from the group consisting of inflammatory, autoimmune, allergic, and infectious diseases, and rejection of transplanted organs.

In another aspect, the invention provides a method for producing a polypeptide with immunosuppressive activity, comprising the steps of: (a) providing a transformed host cell; (b) culture said cell under conducive conditions for production of the polypeptide; and (c) isolation of said polypeptide from said cell or from the culture media surrounding the said cell. In one embodiment, the polypeptide being produced is providing with a tag.

In another aspect, is provided a method for preventing or treating conditions requiring immunosuppression, comprising administering a therapeutically effective amount of immunosuppressive polypeptide to an individual in need of said prevention or treatment. In one embodiment, the conditions requiring immunosuppression are selected from the group consisting of inflammatory, autoimmune, allergic, and infectious diseases, and rejection of transplanted organs. In further embodiments, the inflammatory disease is selected from the group consisting of idiopathic, chronic and acute inflammatory diseases; autoimmune diseases are selected from the group consisting of chronic rheumatoid arthritis, juvenile rheumatoid arthritis, systemic lupus erythematosus, scleroderma, Crohn's disease, mixed connective tissue disease, dermatomyositis, Sjögren's syndrome, Bechet's disease, multiple sclerosis, primary myxedema, Hashimoto's disease, psoriasis, pernicious anemia, Idiopathic thrombocytopenic purpura, vasculitis, heparin-induced thrombocytopenia, uveitis, hemolytic anemia, thrombocytopenic purpura, pemphigus vulgaris, vasculitis caused by antineutrophil cytoplasmic antibodies, Goodpasture's syndrome, acute rheumatic fever, myasthenia gravis, hyperthyroidism, insulin-resistant diabetes, polyarteritis nodosa, post-streptococcal glomerulonephritis, serum sickness and sepsis; and the allergic diseases are selected from the group consisting of atopic dermatitis, asthma, bronchitis, rhinitis, hay fever, urticaria, angioedema, contact dermatitis, allergic gastroenteropathy, anaphylaxis, hemolytic anemia and hemolytic disease of the newborn, sinusitis, rheumatic fever, hypersensitive pneumonitis, streptococcal glomerulonephritis and allergic alveolitis.

BRIEF DESCRIPTION OF THE DRAWINGS

FIG. 1: Chromatographic profile of the first step of purification of inhibitory factor of humoral immune response to *Lachesis muta* heterologous antigens in molecular exclusion column (Superose 12) on FPLC system.

Figure 2:
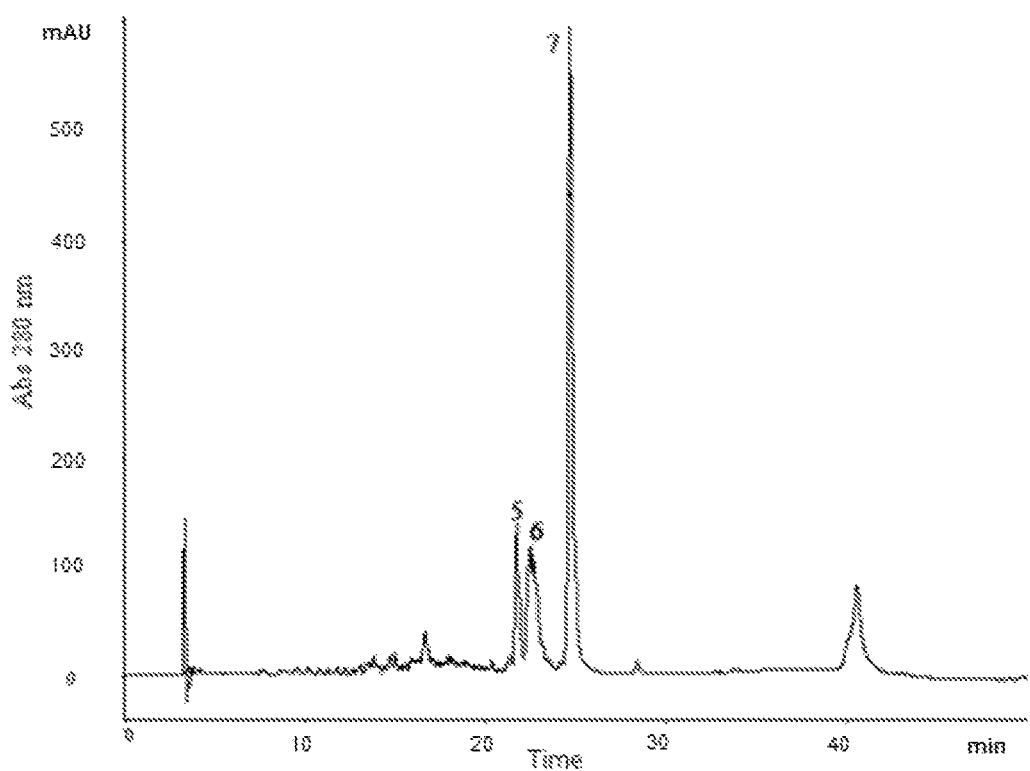

FIG. 2: Chromatographic profile of the purification of the inhibitory factor of humoral immune response to *Lachesis muta* heterologous antigens in Wide-Pore Butyl C18 in HPLC system.

Figure 3:
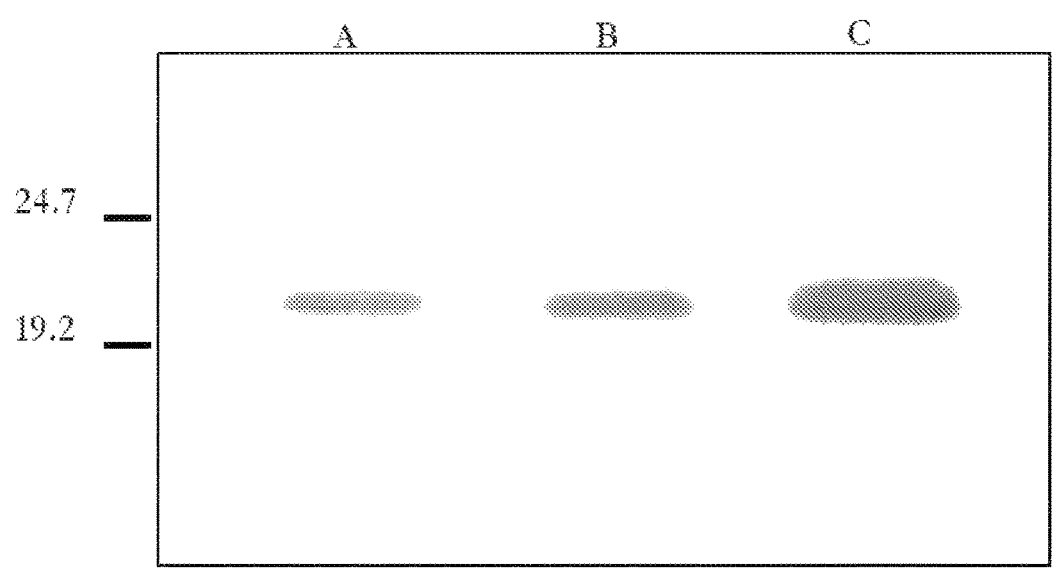

FIG. 3: Analysis of purity of inhibitory factor of humoral immune response to *Lachesis muta* heterologous antigens by SDS-PAGE. Samples of 1 (A), 2 (B) and 3 μg (C) of the factor were analyzed.

FIG. 4: Identity analysis of the inhibitory factor of humoral immune response to *Lachesis muta* heterologous antigens. The amino acid sequence shown is SEQ ID NO:26. The peptide sequences of the purified factor identical to LHF-II are highlighted.

Figure 5:
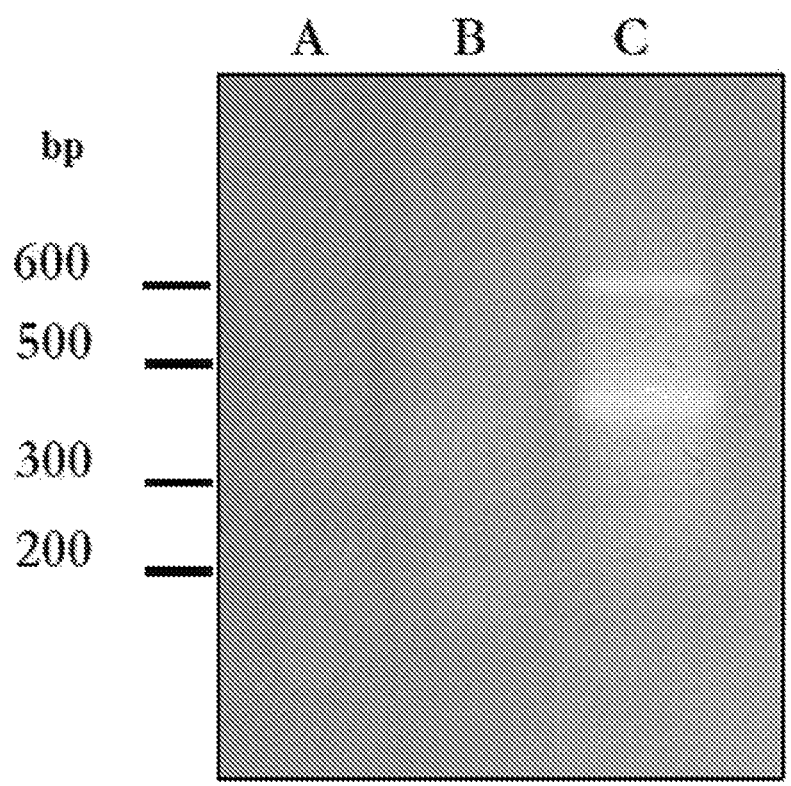

FIG. 5: PCR products obtained during the cloning procedure. (A) negative control; (B) product of the first PCR reaction; (C) product of the second PCR reaction using the PCR product obtained in the first reaction as template.

Figure 6:
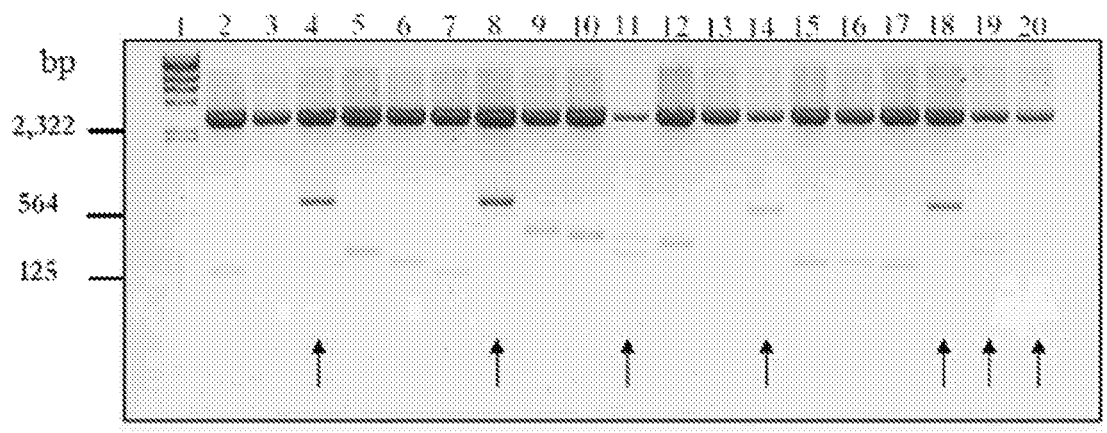

FIG. 6: Restriction enzyme analysis of the cloned PCR products. 1—Molecular weight standard-lambda phage DNA digested with Hind III; 2 to 20—digested clones with EcoR-I restriction enzyme.

FIG. 7: cDNA sequence (SEQ ID NO: 1) obtained from producer clone of recombinant polypeptide of SEQ ID NO: 2.

FIG. 8: Alignment of the recombinant polypeptide (SEQ ID NO: 2) of the invention with proteins of the reprolysine family. Q90392.1, amino acids 6-202 of SEQ ID NO:23; IIAG_A, amino acids 6-202 of SEQ ID NO:24; A92032.1, amino acids 193-389 of SEQ ID NO:25; LHF-II, amino acids 4-200 of SEQ ID NO:26; AAB26922.1, amino acids 7-203 of SEQ ID NO:27; Q98995.1, amino acids 201-397 of SEQ ID NO:28; P20164.4, amino acids 7-203 of SEQ ID NO:29; P20165.3, amino acids 6-201 of SEQ ID NO:30; and P15503.3, amino acids 197-391 of SEQ ID NO:31.

Figure 9:
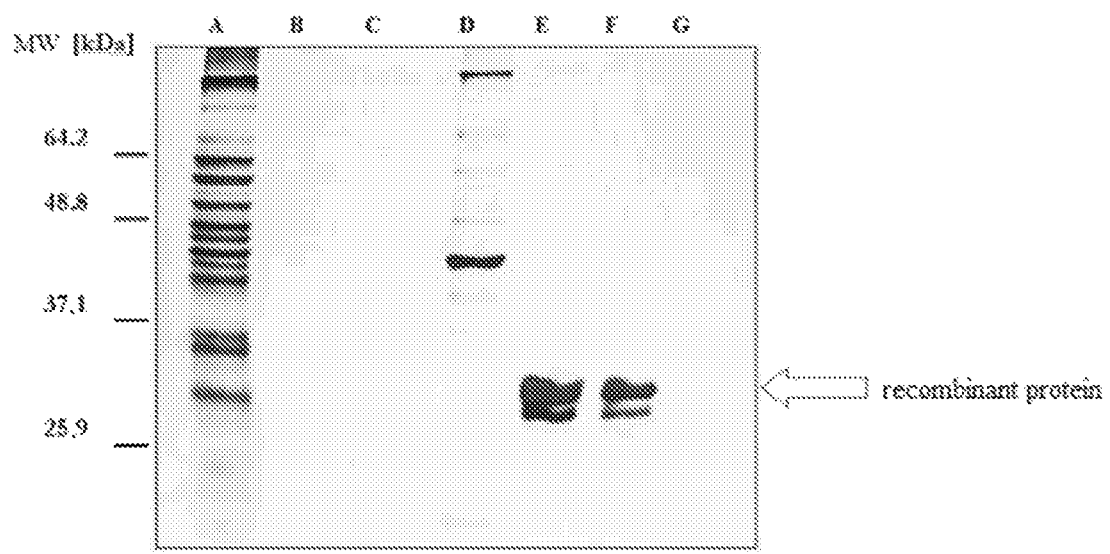

FIG. 9: Analysis of purification steps of the recombinant polypeptide (SEQ ID NO: 3). Amount per sample—20 μg; (A) Eluate; (B) Equilibration buffer (0.002 M $Na_3PO_4$, 0.5 M NaCl, pH 7.8); (C) wash buffer (0.002 M $Na_3PO_4$, 0.5 M NaCl, pH 6.0); (D) Wash Buffer with 30 mM imidazole; (E) Wash Buffer with 60 mM imidazole; (F) Wash buffer with 400 mM imidazole.

Figure 10:
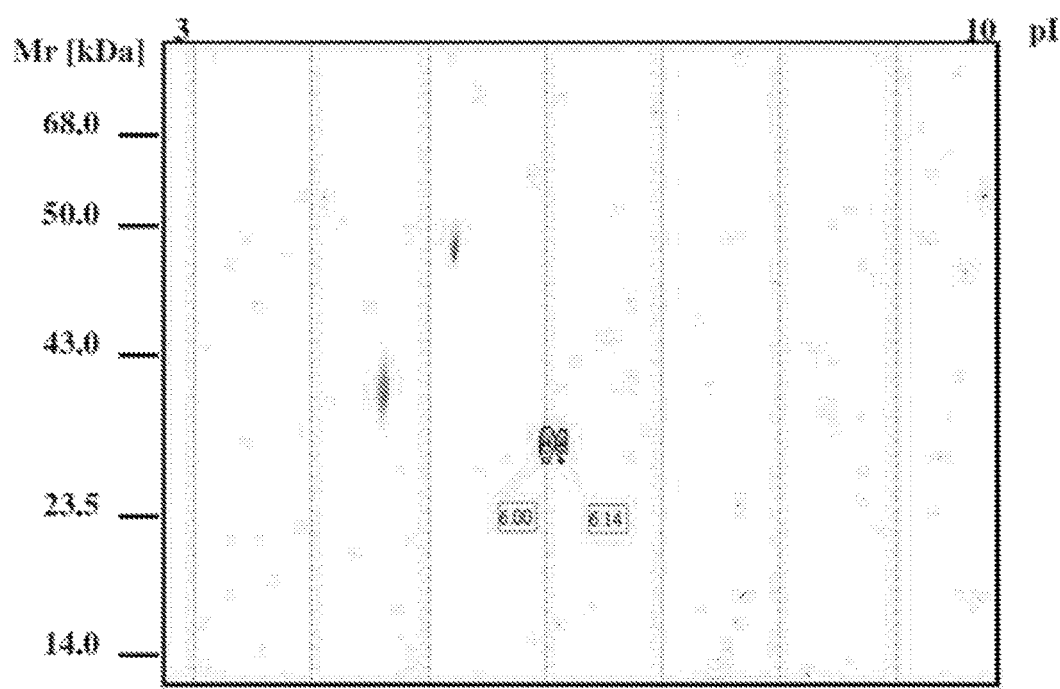

FIG. 10: Recombinant polypeptide analysis (SEQ ID NO: 3) by isoelectric focus in two-dimensional electrophoresis.

Figure 11:
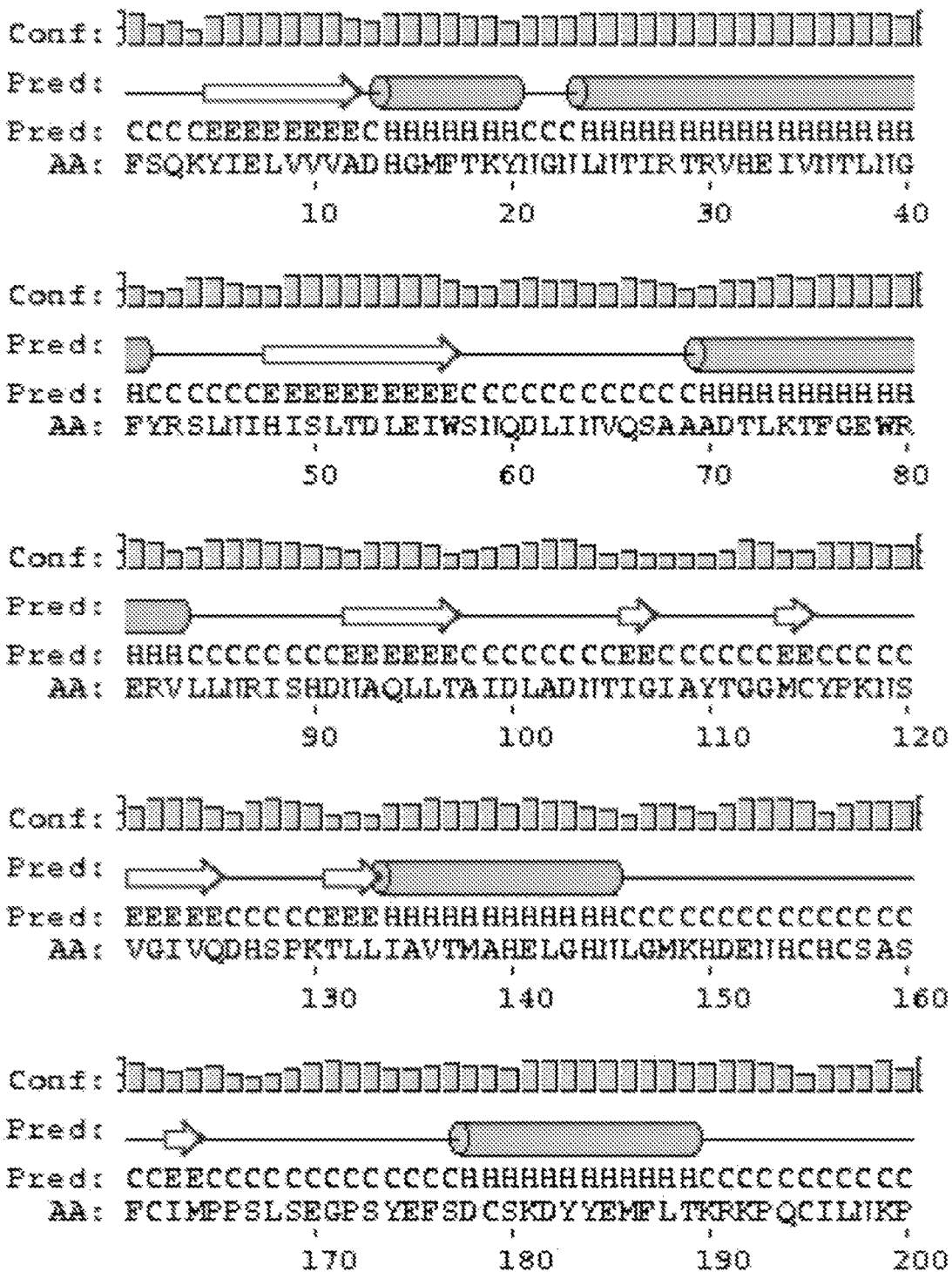

FIG. 11: Prediction of recombinant polypeptide (SEQ ID NO:2) secondary structure. H, helix; C, coil; E, strand.

Figure 12:
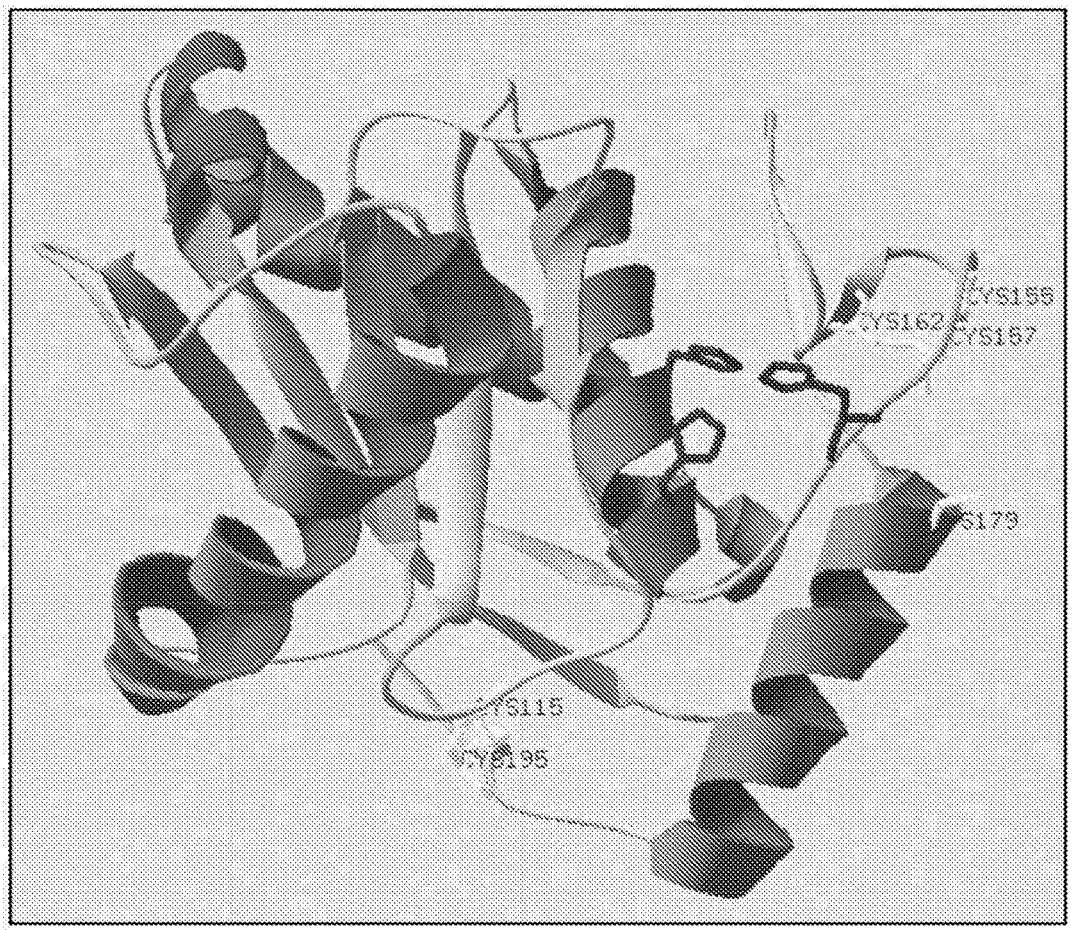

FIG. 12: Prediction of recombinant polypeptide tertiary structure (SEQ ID NO: 2).

Figure 13:
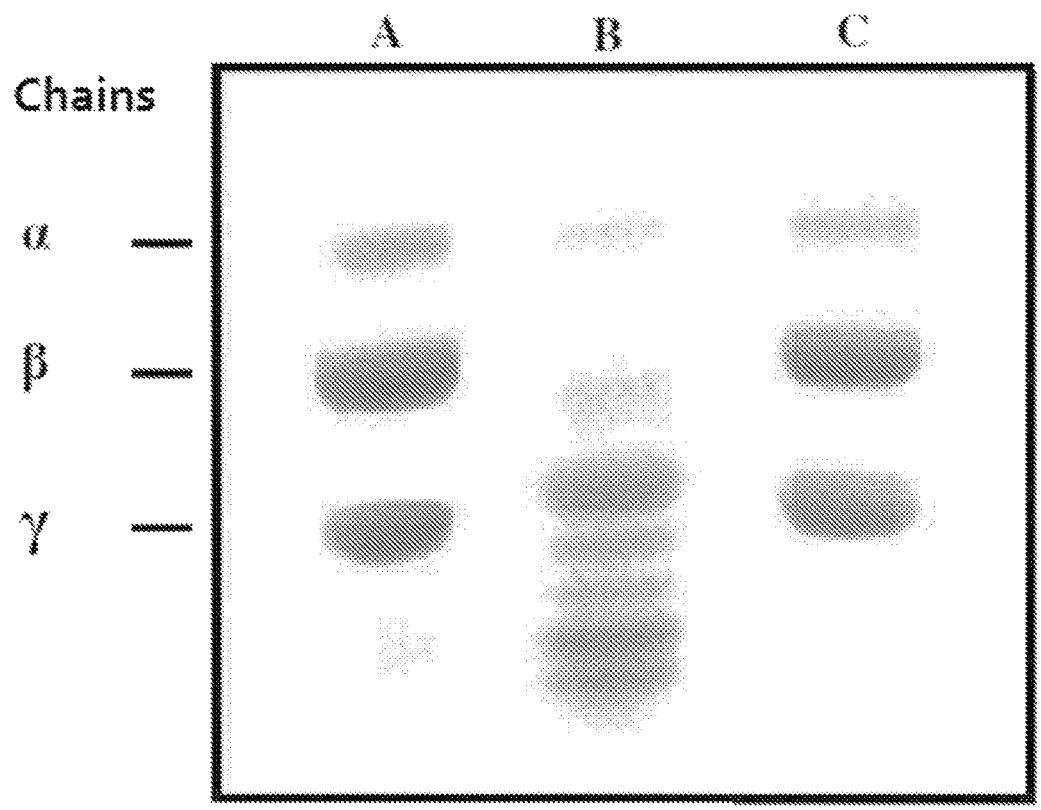

FIG. 13: Fibrinogenolytic assay. (A) Fibrinogen; (B) Fibrinogen+venom; (C) Fibrinogen+recombinant polypeptide (SEQ ID NO: 3).

Figure 14:
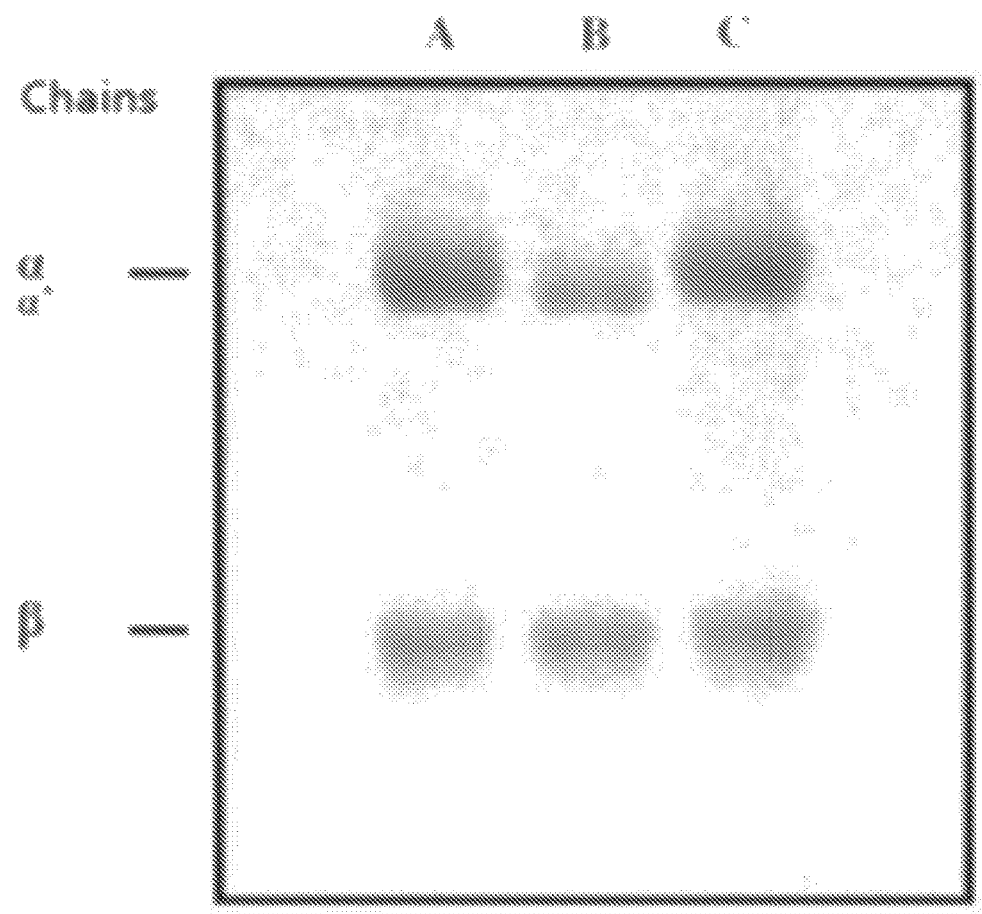

FIG. 14: Cleavage evaluation of C3 component. (A) Human C3; (B) human C3+venom; (C) human C3+recombinant polypeptide (SEQ ID NO: 3).

Figure 15:
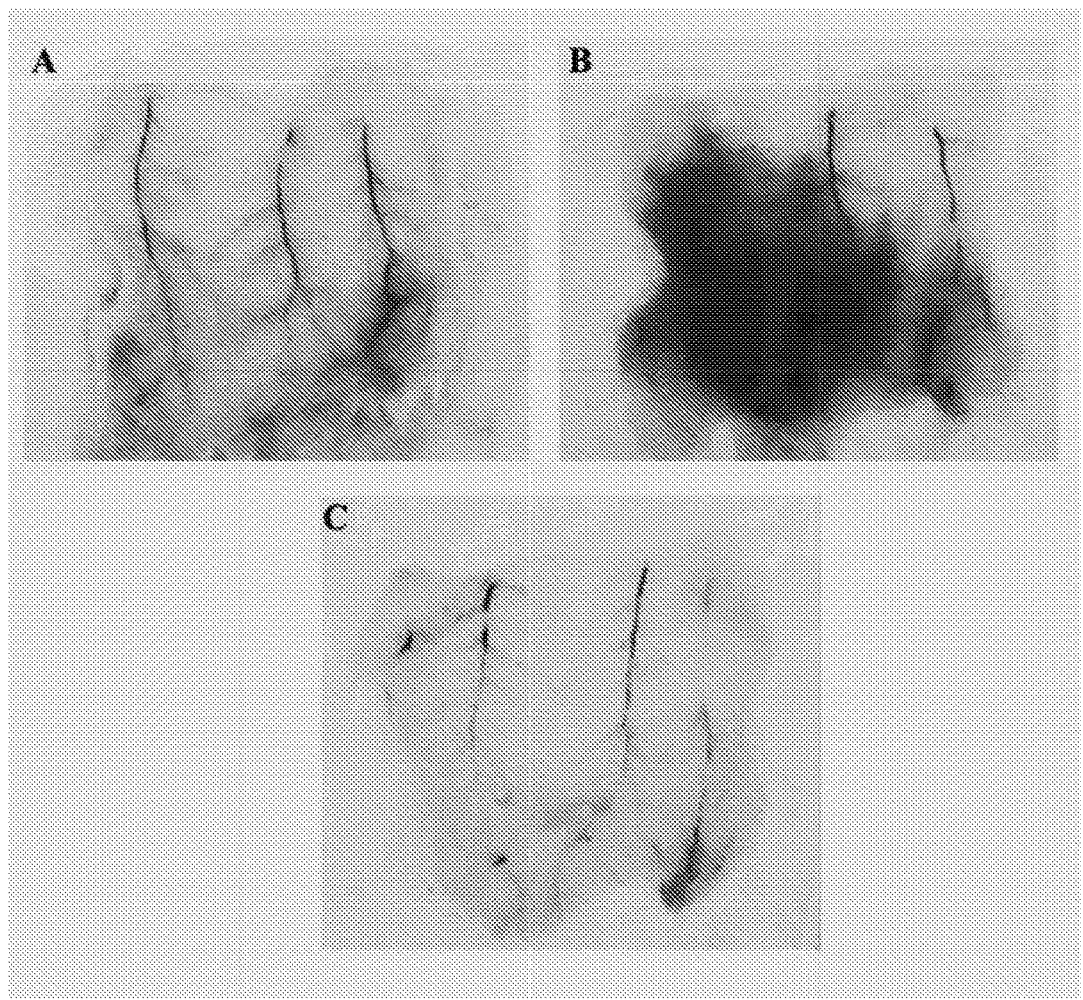

FIG. 15: Evaluation of the haemorrhagic activity (recombinant polypeptide SEQ ID NO: 3).

Figure 16:
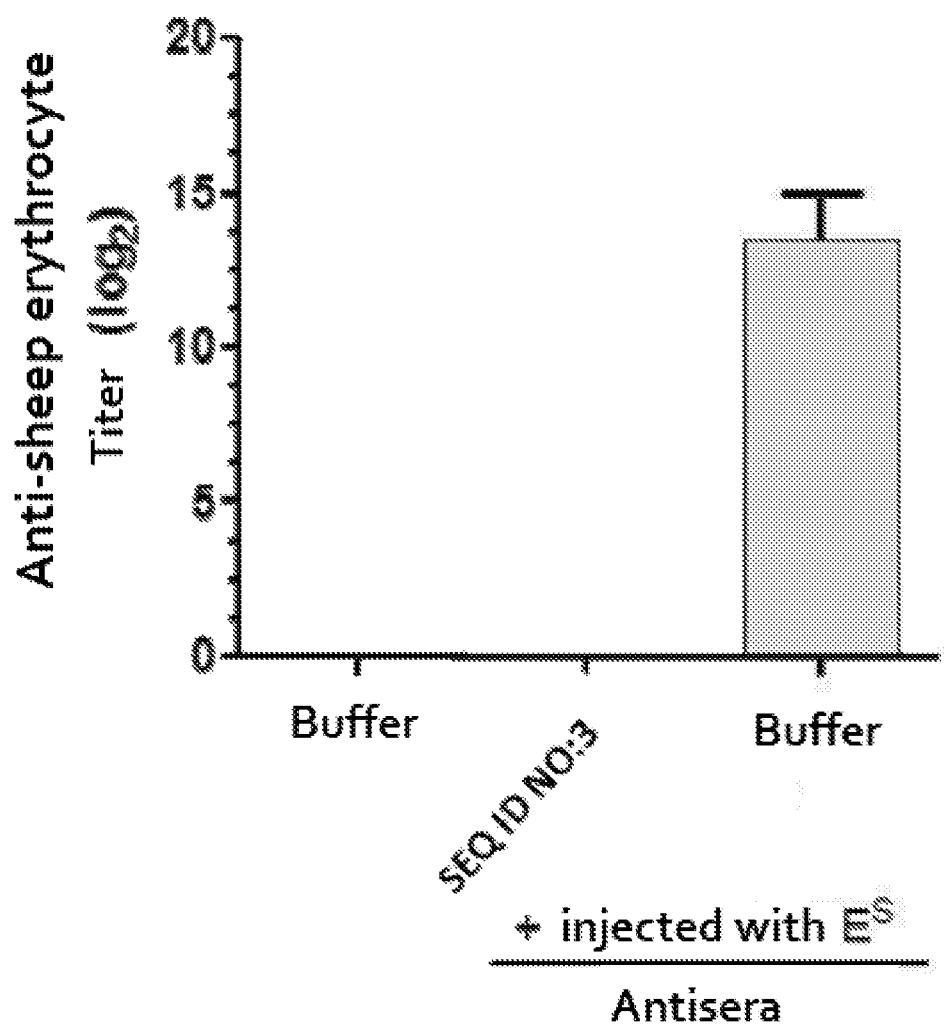

FIG. 16: Immunosuppressive activity of the recombinant polypeptide (SEQ ID NO: 3) over antibody production against particulate antigens.

Figure 17:
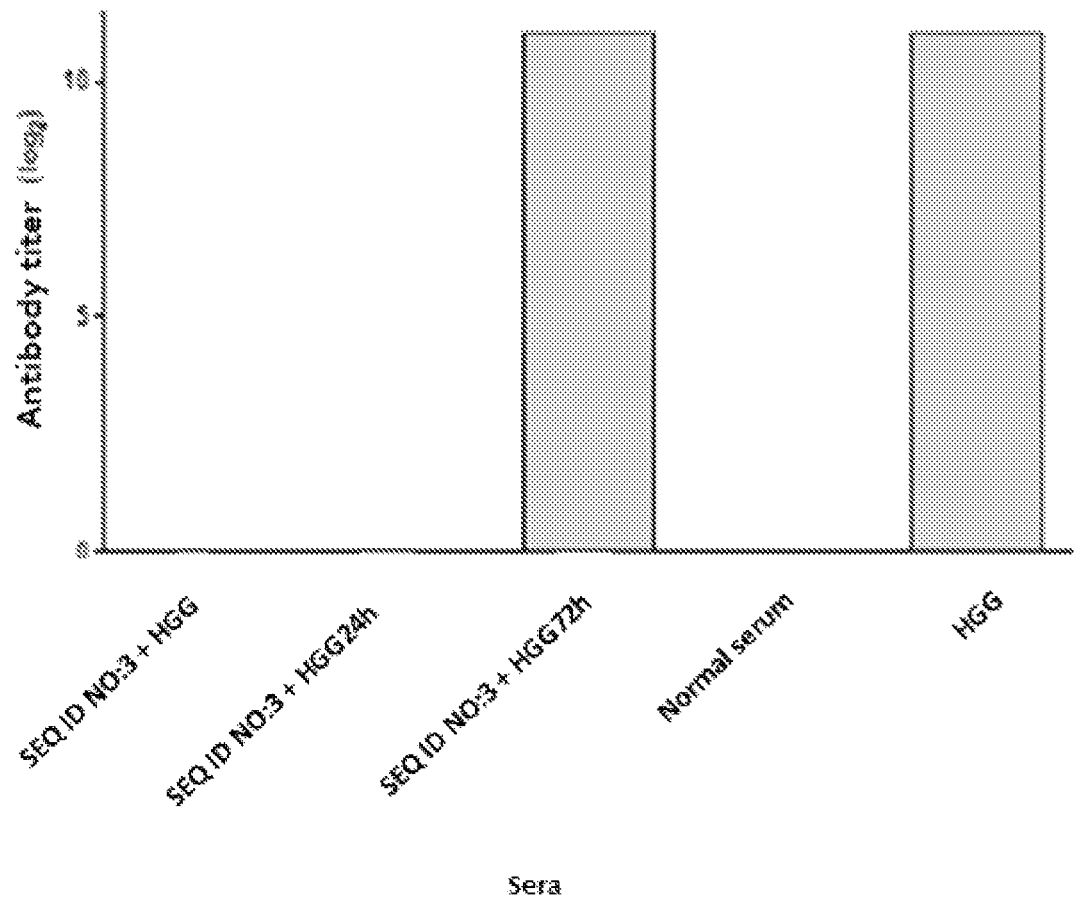

FIG. 17: Immunosuppressive activity of the recombinant polypeptide (SEQ ID NO: 3) over antibody production against soluble antigens.

Figure 18:
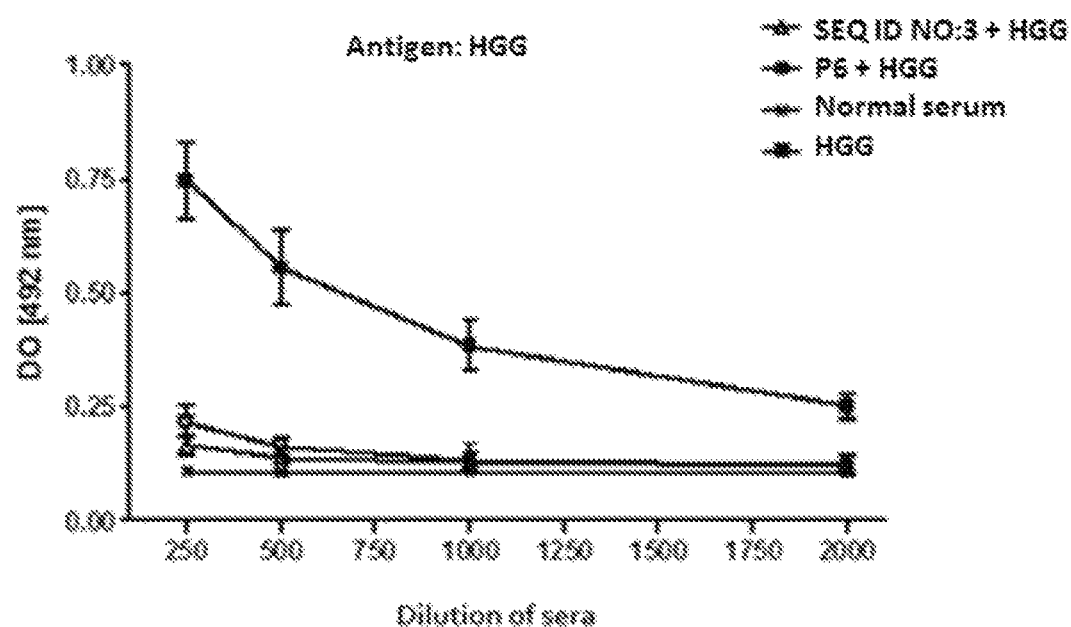

FIG. 18: Immunosuppressive effect of polypeptide P6 (SEQ ID NO: 9) and recombinant polypeptide (SEQ ID NO: 3).

Figure 19:
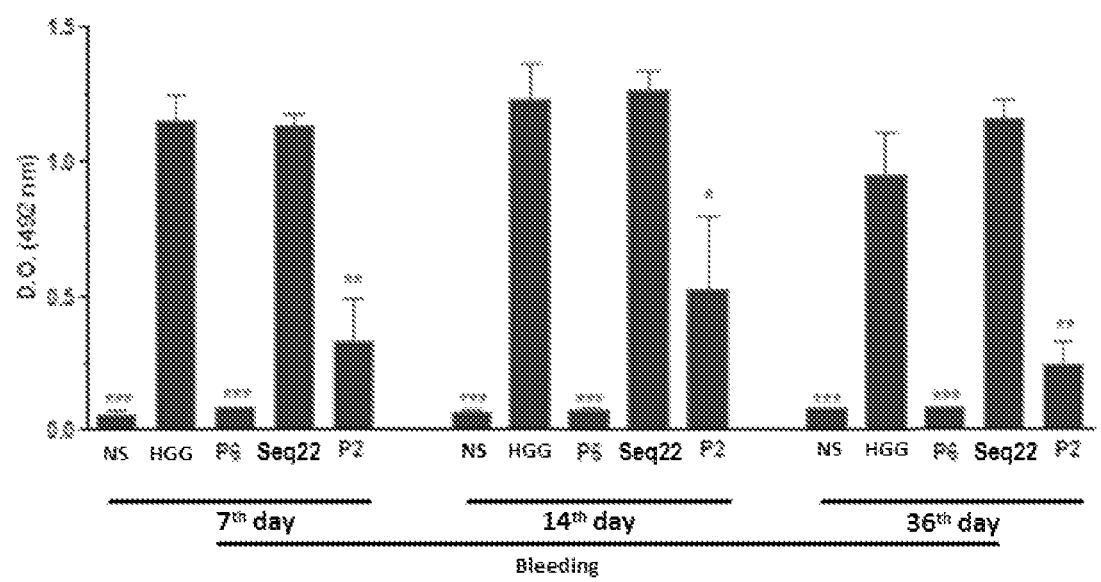

FIG. 19: Graphic representation of the immunosuppressive effect of polypeptides P6 (SEQ ID NO: 9) and P2 (SEQ ID NO: 5) on days 7, 13 and 36 post-treatment.

DEFINITIONS

In order to guarantee a better understanding of the invention's scope, without it being a limiting factor, the technical terms of the related technology fields, as used in this invention, are defined as follows.

The terms "nucleic acid" and "polynucleotide" are used interchangeably and refer to RNA and DNA. The polynucleotides may be single or double stranded. Non-limiting examples of polynucleotides include genes, gene fragments, exons, introns, messenger RNA, siRNA, miRNA, complementary DNA, genomic DNA, synthetic DNA, recombinant DNA, cassettes, vectors, probes and primers. The term "recombinant DNA" refers to any artificial nucleotide sequence which results from the combination of DNA sequences from different sources.

The term "degenerated nucleotide sequence" denotes a nucleotide sequence including one or more degenerated codons when compared to a reference nucleic acid that encoding a given polypeptide. Degenerated codons contain different nucleotides triplets, but encode the same amino acid residue (e.g., both GAU and GAC encode Asp).

The term "therapeutically effective amount" refers to an amount of protein or polypeptide that provides immunosuppressive activity when administered in accordance to the appropriate dose and administration route.

The term "pharmaceutically acceptable salt" includes salts usually used to form metal salts or acid addition salts. The nature of the salt is not critical, if it is pharmaceutically acceptable. Pharmaceutically acceptable salts of the invention's polypeptides can be obtained from acids or organic or inorganic bases. Said salts can be obtained by well-known conventional methods in the art.

The term "conditions requiring immunosuppression" refers to clinical conditions where there is an inadequate immune response, in either strength (for example, hypersensitivity reactions) or specificity (e.g., autoimmune diseases). In these cases, the clinical condition benefits from the effects of immunosuppression, that prevents or reduces the progression of inadequate immune response, preventing cellular and tissue damages and other losses that may be related.

The term "pharmaceutically acceptable carriers or excipients" refers to ingredients compatible with other ingredients of pharmaceutical preparations which show no therapeutic effect and are not harmful to humans or animals.

The term "individual" refers to humans and animals. Preferably, the individual is a human being.

The term "fragment" refers to a specific region of the nucleotide or polypeptide sequence corresponding to the sequences shown herein that exert the desired immunosuppressive function.

The term "homology" refers to cases in which the identity between the sequences leads to involvement of common ancestry between them.

The term "identity" is defined as the degree of equality between DNA or amino acid sequences when compared nucleotide by nucleotide or amino acid by amino acid with a reference sequence.

The term "similarity" is defined as the degree of equality between two or more DNA or amino acid sequences compared nucleotide-by-nucleotide or amino acid-by-amino acid.

The term "percentage of sequence identity" refers to comparisons among polynucleotides and polypeptides, and is determined by two sequences ideally aligned under certain comparison parameters. This alignment may include gaps, producing intervals when compared to the reference sequence, which facilitate proper comparison. In general, the identity percentage calculation considers the number of positions where the same nucleotide or amino acid occur in the sequences compared to the reference, being performed with various sequence comparison algorithms and known programs in the state of art. Such algorithms and programs include, but are not limited to, TBLASTN, BLASTP, FASTA, TFASTA, CLUSTALW, FASTDB.

In this invention the similarity is estimated using method and comparison parameters equivalent to those used to estimate the percentage of sequence identity without, however, performing a comparison in relation to a reference sequence. To estimate the percentage of similarity, comparisons among polynucleotides or polypeptides are performed between two or more ideally aligned sequences.

For purposes herein, the term "complementary" is defined as the ability of the sense strand (direction 5'→3') of a nucleotide segment to hybridize itself with an antisense strand (the 3'→5') of another segment nucleotide, under appropriate conditions to form a double helix.

The term "Polymerase Chain Reaction" or the acronym PCR refers to a method in which a nucleic acid fragment is amplified as described in U.S. Pat. No. 4,683,195. Usually, the information contained at the 5' and 3' ends of the sequence of interest is used for the design of initiator oligonucleotides or primers, which comprehend about 8 synthetic nucleotides. These primers show complementary sequences to the sequence to be amplified. The PCR can be used to amplify sequences from RNA, DNA or cDNA.

An "expression cassette" refers to a nucleic acid construction comprising a coding region operably linked to a regulatory region so that when inserted into a host cell, results in transcription and/or translation of RNA or polypeptide, respectively. Usually, an expression cassette is composed of or is comprised by a promoter, which allows the transcription to initiate, a nucleic acid, according to the invention, and a transcription terminator. The term "operably linked to" indicates that elements are combined so that expression of the coding sequence is under the transcriptional control of the promoter and/or signal peptide. Typically, the promoter sequence is placed upstream of the gene of interest, from a distance compatible with the expression control. Similarly, the signal peptide sequence is generally fused upstream to the sequence of the gene of interest and in phase with it, and downstream of any promoter. Spacing sequences may be present between the regulatory elements and the gene, as it does not prevent the expression and/or sorting. In one embodiment, the said expression cassette comprises at least one enhancer sequence activator operably linked to the promoter.

The term "vector" refers to nucleic acid molecules designed to transport, transfer and/or store genetic material, as well express and/or integrate the genetic material to the host cell chromosomal DNA, such as plasmids, cosmids, artificial chromosomes, bacteriophages and other viruses. The vector is usually composed of at least three basic units, the origin of replication, a selection marker and multiple cloning sites.

The vectors used in this invention preferably present at least one "selection marker", that is a genetic element that allows the selection of genetically modified organisms/cells. Such markers include genes for antibiotic resistance such as, but not limited to, ampicillin, chloramphenicol, tetracycline, kanamycin, hygromycin, bleomycin, phleomycin, puromycin and/or phenotype complementing genes, such as, but not limited to, methotrexate, dihydrofolate reductase, ampicillin, neomycin, mycophenolic acid, glutamine synthetase.

The term "expression vector" refers to any vector that is capable of transporting, transferring and/or storing the genetic material and which, once in the host cell, is used as a source of genetic information for producing one or more gene products (gene expression).

In addition, the expression vectors of this invention may include one or more regulatory nucleotide sequences to control gene replication, transfer, transport, storage, and expression of genetic material, such as replication origin, selection marker, multiple cloning site, promoter (e.g., T7 pol, pL and pR phage lambda, SV40, CMV, HSV tk, PGK, T4 pol, or EF-1 alpha, and its derivatives), ribosome binding site, RNA splice site, polyadenylation site, signal peptide for secretion, and gene transcription terminator sequence. However, the expression vectors of this invention are not limited to them. The technique of incorporating control sequences in a vector is well characterized in the state of the art.

The expression vector used in this invention may also have enhancer sequences, also called "cis" elements, which can positive or negatively influence the promoter dependent gene expression.

A "coding sequence" refers to a nucleotide sequence that is transcribed into mRNA (messenger RNA) and translated into a polypeptide when under the control of appropriate regulatory sequences. Coding sequence boundaries are determined by a translation start codon at the 5' end of the DNA sense strand and a translation stop codon at the 3' end of the DNA sense strand. As a result of the genetic code degeneration, other DNA sequences can encode the same polypeptide sequence. Therefore, it is considered that such degenerated substitutions in the coding region are inserted into the sequences disclosed herein.

The term "promoter" is a minimal DNA sequence sufficient to direct gene transcription, i.e., a sequence that directs the binding of RNA polymerase enzyme thereby promoting the synthesis of messenger RNA. Promoters may be specific to the cell type, tissue type and species, besides being modulated, in some cases, by regulatory elements in response to any physical or chemical external agent called inductor.

The terms "transformation" and "transfection" refer to the act of inserting a vector, or other carrier vehicle of exogenous genetic material, into a host cell, prokaryotic or eukaryotic, for transportation, transfer, storage, and/or gene expression of the genetic material of interest.

The term "recombinant expression" refers to expression of the recombinant polypeptide in host cells.

The term "host cell" refers to cells which will receive the genetic material through a vector and/or cells that have already received genetic material through a vector (transformed or transfected cells). These host cells may be either of prokaryotic (prokaryotic microorganisms) or eukaryotic (or eukaryotic microorganisms) origin.

In this application, the terms "peptide", "polypeptide" or "protein" may be used interchangeably, and refer to a polymer of amino acids connected by peptide bonds, regardless of the number of amino acid residues that constitutes the chain. The polypeptides, as used herein, include "variant" or "derivative" thereof, which refers to a polypeptide which includes variations or modifications, e.g., substitution, deletion, addition or chemical modification in its amino acid sequence, compared to the reference polypeptide, since the derived polypeptide presents immunosuppressive activity, stability, half-life, pharmacokinetic and/or physical-chemical characteristics equal or superior to what was initially observed for the original polypeptide. Examples of chemical modifications are glycosylation, PEGylation, PEG alkylation, alkylation, phosphorylation, acetylation, amidation etc. The amino acids of polypeptides of the present invention, depending on the orientation of the amino group attached to the alpha carbon, can belong to L or D series. The polypeptide can be produced artificially from cloned nucleotide sequences through recombinant DNA technique ("recombinant polypeptide"), or can be chemically synthesized through known chemical reactions ("synthetic polypeptide").

The term "amino acid substitutions" refers to replacement of at least one amino acid residue in the polypeptide, aiming the production of derivatives with immunosuppressive activity, stability, half-life, pharmacokinetic and/or physical-chemical characteristics equal or superior to what was initially observed on the original polypeptides. The substitute amino acid may be natural, modified or unusual.

Regarding this, the term "conservative amino acid substitution" refers to replacement of amino acids in a polypeptide by those with similar side chains, therefore, with very close physical-chemical properties. For example, the exchange of an alanine for a valine, leucine or isoleucine is considered conservative, since the amino acids involved have as a common characteristic an aliphatic side chain. The group containing a basic side chain as characteristic comprises lysine, arginine and histidine. The group containing sulfur in the side chain comprises the amino acids cysteine and methionine. The amino acids phenylalanine, tyrosine and tryptophan contain an aromatic side chain. Asparagine and glutamine are part of amino acids containing amide in the side chain, while serine and threonine contains a hydroxyl bound to its aliphatic side chain. Other examples of conservative substitution include the substitution of a nonpolar or hydrophobic amino acid as isoleucine, valine, leucine or methionine for another nonpolar as well. Likewise, the invention described herein comprises the substitution of polar or hydrophilic amino acids such as arginine for lysine, glutamine for asparagine, and threonine for serine. Additionally, substitution between basic amino acids such as lysine, arginine or histidine, or substitution of amino acids like aspartic acid or glutamic acid is also contemplated. Examples of conservative substitution of amino acids are: valine for leucine or isoleucine, phenylalanine for tyrosine, lysine for arginine, alanine for valine, and asparagine for glutamine. In this invention, substitution matrices used in the amino acids protein alignment as BLOSUM62 may also be used to determine which amino acids are most likely to replace a residue in a given peptide sequence (HENIKOFF & HENIKOFF. 1992 *PNAS.* 89:10915-10919).

In addition, illustrative examples of modified or uncommon amino acids include 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminoheptanoic acid, 2-aminopimelic acid, 2,4-diaminobutyric acid, desmosine, 2,2-diaminopimelic acid, 2,3-diaminopropionic acid, N-ethylglycine, N-etilasparagine, hydroxylysine, allo-hydroxylysine, 3-hydroxyproline, 4-hydroxyproline, isodesmosine, allo-isoleucine, N-methyl glycine, N-methyl isoleucine, 6-N-methyl lysine, N-methyl valine, norvaline, norleucine, omithine, etc.

The objects of this invention will be better understood from the detailed description of the invention and the attached claims.

DETAILED DESCRIPTION OF THE INVENTION

This invention relates to a recombinant polynucleotide illustrated, but not limited to, the sequence shown in SEQ ID NO: 1, and includes nucleic acid sequences comprising SEQ ID NO: 1, sequences encoding amino acid 85 to amino acid 117 of SEQ ID NO: 2, and the sequences encoding the polypeptides of SEQ ID NOs: 2-15. Also, are included the variants of SEQ ID NO: 1, with one or more bases deleted, substituted, inserted, added or chemically modified, including non-natural or modified nucleotide bases comprising, for example, a modified linkage, a modified base of purine or pyrimidine, or a modified sugar, such encoding variants for the polypeptides herein defined. This invention also provides polynucleotides which are at least 70% identical (such as at least 75%, 80%, 85%, 90%, 91%, 92%, 93%, 94%, 95%, 96%, 97%, 98% or 99% identical) to a nucleic acid molecule shown in SEQ ID NO: 1.

The polynucleotide according to the invention can be deduced from the sequence of the polypeptide as defined in SEQ ID NOs: 2-15, and the use of codons may be adjusted according to the host cell in which the nucleic acid must be transcribed. These steps can be carried out according to well-known methods to a person skilled in the art, some of which are described in the reference manual Sambrook et al. (SAMBROOK et al, 2001).

In this regard, different species can exhibit a preferred "codon usage". See Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term used in the art to refer to codons that are most frequently used in cells of certain species. For example, the amino acid threonine (Thr) may be encoded by ACA, ACC, ACG, or ACT, but in mammalian cells ACC is the most commonly used codon. In other species, for example, different Thr codons may be preferential. Preferential codons for a particular species can be introduced into the polynucleotides of this invention by a variety of methods known in the art. Introduction of preferential codon sequences into a recombinant DNA can, for example, enhance production of the polypeptide by making the translation more efficient in a given cell type. Thus, the polynucleotide sequences of the invention can be optimized for different species.

The nucleic acids of this invention are obtained by known methods in the art such as those described by Sambrook et al. (2001). For example, additional sequences can be identified and functionally noted by sequence comparison. Therefore, a person skilled in the art can promptly identify a sequence functionally equivalent to the molecules of the invention into a suitable database such as GenBank, using sequence analysis software and publicly available parameters.

Additionally, for example, DNA as whole or portions of it can be obtained. For example, all the molecule or portions comprising the sequence shown in SEQ ID NO: 1 can be used as a hybridization probe to screen a genomic library or a cDNA library, e.g., snakes of the genus *Lachesis* by hybridization under stringent conditions of nucleic acid probes marked with radioisotopes with nucleic acids immobilized on nylon membranes or nitrocellulose. The nucleotide sequences of genomic or cDNA library, which hybridize to specific probe, can then be subcloned into appropriate vector and sequenced for analysis and obtaining of coding regions of the invention's immunosuppressive polypeptides.

The term "stringent conditions" denotes parameters to which the art is familiar. The stringency of a hybridization reflects the degree of sequence identity of the nucleic acids involved, in a way that the higher the stringency, the more similar are the two polynucleotide strands. The stringency is influenced by several factors, including the number of incubations, temperature, salt concentration and composition, organic and inorganic additives, solvents etc. The stringent conditions are exemplified by a temperature of about 5° C. to 20° C. lower than the melting temperature (Tm) for the specific sequence at a defined ionic strength and pH. The Tm is the temperature at which 50% of the target sequence hybridizes to a complementary sequence under conditions of defined ionic strength and pH. Nucleic acid molecules that hybridize under stringent conditions will typically hybridize to a nucleic acid based on both the entire cDNA and the selected portions thereof.

Preferably, "stringent conditions" refers to parameters which the art is familiar, such as hybridization in 3.5×SSC, Denhardt's 1× solution, 25 mM sodium phosphate buffer (pH 7.0), 0.5% SDS, and 2 mM EDTA for 18 hours at 65° C., followed by 4 washes of the membrane at 65° C. for 20 minutes in 2×SSC and 0.1% SDS and a final wash, for up to 20 minutes in 0.5×SSC and 0.1% SDS or 0.3×SSC and 0.1% SDS for greater stringency, and 0.1×SSC and 0.1% SDS for even greater stringency. The conditions may be modified, as long as the degree of stringency is equal to the provided herein. For identification of less closely related sequences, washes can be performed at a lower temperature, e.g. 50° C. In general, stringency is increased by increasing the wash temperature or decreasing the concentration of SSC.

In another example, the nucleic acid molecules of the invention can be obtained by a reverse-transcription reaction followed by PCR amplification. Both oligo-dT and random primers may be employed in reverse transcription reactions to prepare single-stranded cDNAs from RNA isolated from *L. muta* snake, containing the sequences of interest. RNA can be isolated by known methods using Trizol reagent (GIBCO-BRL/Life Technologies, Gaithersburg, Md.).

Gobinda et al. (PCR Methods Applic. 2:318-22, 1993), describes PCR restriction site (restriction-site PCR) as a direct method that uses universal primers to obtain unknown sequences adjacent to a known locus. First, genomic DNA is amplified in the presence of an adapter-primer that is homologous to an adapter sequence attached to the ends of genomic DNA fragments and in the presence of a primer specific to a known region. The amplified sequences are subjected to a second round of PCR with the same adapter-primer and another specific primer, internal to the first one. Products of each round of PCR are transcribed with a suitable RNA polymerase and sequenced using a reverse transcriptase.

Still illustratively, the inverse PCR permits acquisition of unknown sequences starting with primers based on a known region (TRIGLIA, T. et al. *Nucleic Acids Res.* 16: 8186, 1988). The method uses several restriction enzymes to generate a fragment in the known region of the gene. The fragment is then cyclized by intramolecular bonding and used as template for PCR. Divergent primers are designed from the known region.

Besides, it is known that sequences with lower degrees of identity may also be obtained with the use of degenerated primers and PCR-based methodologies.

Typically, the nucleic acid sequence of a primer useful to amplify a nucleic acid molecule through PCR may be based on the amino acid sequences of polypeptides of the invention represented, for example, by SEQ ID NOs: 2 or 3.

Furthermore, this invention relates to an expression cassette comprising a nucleic acid according to the invention operatively linked to sequences required for its expression. Typically, the coding and regulatory regions are heterologous to each other.

In addition, this invention relates to an expression vector comprising a nucleic acid or an expression cassette according to the invention.

This expression vector can be used to transform a host cell allowing the expression of the nucleic acid according to the invention in the said cell.

Advantageously, the expression vector comprises regulatory elements, which allow expression, and nucleic acid elements that permit selection in a host cell according to the invention. The methods for selecting these elements function in the host cell, in which expression is desired, are well known to one versed in the art and widely described in the literature.

The vectors may be constructed by the classical techniques of molecular biology, well known in the art. Non-limiting examples of suitable expression vectors for expression in host cells are plasmids and viral or bacterial vectors.

This invention relates to the use of a nucleic acid, expression cassette or an expression vector, according to the invention, to transform or transfect a cell. The host cell can be transformed/transfected stably or transiently, and the nucleic acid, cassette or vector can be contained in the cell in the form of episome or under chromosomal form.

The nucleic acid, expression cassette or vector is inserted into competent prokaryotic or eukaryotic host cells. Recombinant clones are selected and then subjected to analysis by restriction enzymes and DNA sequencing, confirming the cloned sequence, through methods, kits and equipment widely known by a person skilled in the art.

Thus, the polypeptides of the invention may be prepared using recombinant DNA technology, in which a cassette or expression vector comprising a nucleic acid sequence of the invention, e.g. encoding any of the polypeptides of SEQ ID NOs: 2-15, is operably linked to a promoter. The host cells are cultured under appropriate conditions and the polypeptide is expressed. The host cell may be a cell of bacteria, fungi, plant or animal. The polypeptide is recovered from the culture, wherein the recovery may include a step of polypeptide purification. The recombinant polypeptide obtained is analyzed and treated to be solubilized, when appropriate. The solubilized polypeptide is then purified and characterized biochemically using, for example, methods common to the field of biochemistry such as HPLC, SDS-PAGE, Western Blotting, isoelectric focusing with a pH gradient, circular dichroism. Through these methods, it is possible to determine characteristics such as, for example, the expression yield of the recombinant polypeptide; determining the characteristics of the secondary structures, and other features whose determination is important for the development of a biotechnological drug.

The polypeptides may be expressed "fused" on a tag. The term 'tag' refers to embedded coding sequences near the multiple cloning site of an expression vector, allowing its concomitant and adjacent translation to the cloned recombinant polypeptide sequence. Thus, the tag is expressed fused to the recombinant polypeptide. Such tags are well known in the art and include compounds and peptides such as poly-histidine, poly-arginine, FLAG, glutathione-S-transferase, maltose binding (MBP) protein, cellulose binding domain (CBD), Beta-Gal, OMNI, thioredoxin, NusA, mistine, chitin binding domain, cutinase, fluorescent compounds (like GFP, YFP, FITC, rhodamine, lanthanide), enzymes (like horseradish peroxidase, luciferase, alkaline phosphatase), chemiluminescent compounds, biotinyl groups, epitopes recognized by antibodies to leucine zipper, c-myc, metal binding domains and binding sites for secondary antibodies.

The polypeptides may also be obtained synthetically using methods known in the art. Direct synthesis of polypeptides of the invention can be accomplished using solid phase synthesis, solution synthesis or other conventional methods, generally using protective groups of α-amino group, the α-carboxyl and/or functional groups of the amino acids side chains. For example, in solid phase synthesis, a suitably protected amino acid residue is bonded through its carboxyl group to an insoluble polymeric support, such as a cross-linked polystyrene resin or polyamide. Methods of solid phase synthesis include both BOC and FMOC methods using tert-butyloxycarbonyl, and 9-fluorenylmethyloxycarbonyl as α-amino protective groups, respectively, both well known to those skilled in the art (SAMBROOK et al., Molecular Cloning.: *A Laboratory Manual*, 2nd edition, Cold Spring Harbor Press, Cold Spring Harbor, N.Y.; AUSUBEL et al., *Current Protocols in Molecular Biology*, John Wiley and Sons, New York. 1995).

The following protective groups can be used for the synthesis of polypeptides of the invention: 9-fluorenylmethyloxycarbonyl (Fmoc), tert-butyloxycarbonyl (Boc), carbobenzyloxy (Cbz), 2-chloro-3-indenylmethoxycarbonyl (Climoc) benz (f) inden-3-yl-methoxycarbonyl (Bimoc), 1,1-dioxobenzo [b] thiophene-2-yl-methoxycarbonyl (Bsmoc), 2,2,2-trichloroethoxycarbonyl (Troc), 2 (trimethylsilyl) ethoxycarbonyl (Teoc), homo-benzyloxycarbonyl (hZ) 1,1-dimethyl-2,2,2,-Trichloroethyloxycarbonyl (TCBoc), 1-methyl-1-(4-biphenyl) ethoxycarbonyl (Bpoc), 1-(3,5-di-t-butylphenyl)-1-methylethoxycarbonyl (t-Bumeoc), 2-(2'- or 4'-pyridyl) ethoxycarbonyl (Pyoc), vinyloxycarbonyl (Voc), 1-isopropylallyloxycarbonyl (IP Aoc), 3-(pyridyl) allyl-oxycarbonyl (Paloc), p-methoxybenzyloxycarbonyl (Moz), p-Nitro-benzyloxycarbonyl (pNZ), 4-azidobenzyloxycarbonyl (AZBZ), benzyl (Bn) MeO, BnO, methoxymethyl (Mom), methylthiomethyl (MTM), phenyldimethylsilyloxymethyl (SMOM), t-butyldimethylsilyl (TBDMS), benzyloxymethyl (BOM), p-methoxybenzyloxymethyl (PMBM), Nitrobenzyloxymethyl (NBOM), anisiloxymetil p-(p-AOM), pBuOCH2O—, 4-pentenyloxymethyl (POM), 2-methoxyethoxymethyl (MEM), 2 (trimethylsilyl) ethoxymethyl (SEM), methoxymethyl (MM), tetrahydropyranyl (THP), —OCOCOph, Acetyl, ClCH2CO2-, —CO2CH2CCl3, 2-(trimethylsilyl) ethyl (TMSE), 2 (p-toluenesulfonyl) ethyl (TSE). (GREENE T. W. & WUTS P. G. M, *Protective groups in organic synthesis*, 3rd ed., John Wiley & Sons, INC, Nova York, EUA, 1999).

The polypeptides of this invention are at least 70%, preferably at least 80% to 85%, preferably at least 90% and more preferably at least 95% to 99% identical to the polypeptide sequences shown in SEQ ID NOs: 2 or 3.

Moreover, the polypeptides of this invention may be of any size. For example, they may be smaller or equal to 300, 200, 100, 50, 25, 10, 5 or 2 amino acids. The appropriate size of the polypeptides may be determined by the skilled person. More preferably, the polypeptide comprises the amino acid sequence as described in SEQ ID NOs: 2 or 3, or fragments thereof provided with immunosuppressive activity.

It is understood that a fragment endowed with immunosuppressive activity is a fragment that, although not comprising the amino acid sequence of SEQ ID NOs: 2 or 3 in its total length, still comprises those regions that are capable of exhibiting an immunosuppressive activity in an individual. Such a fragment may be from 2 to 40, preferably from 3 to 30 contiguous amino acids of the sequences disclosed in SEQ ID NOs: 2 or 3.

For the delimitation of potential useful fragments of this application, the theoretical models of secondary and tertiary structure of polypeptides of the invention are obtained and used for the delimitation and design of useful fragments, with probability of having immunosuppressive activity. More preferably, the theoretical templates polypeptide of SEQ ID NO: 2 are obtained and evaluated.

For purposes of this invention, the exposed regions in the recombinant polypeptide secondary structure (as found in modeling studies) were identified and evaluated. Considering the inventors observation that recombinant polypeptides exhibit low immunogenicity and high suppressive activity of antibody production, and being these functional characteristics maintained even after denaturation by heat (100° C./2 h) or treatment with urea (3 M/72 h and further heating to 100° C./2 h), the hypothesis is that immunosuppressive activity is determined by the polypeptides primary sequence.

Thus, the fragments are provided herein named P1 to P12, which are immunosuppressive polypeptides consisting of amino acid sequences SEQ ID NOs: 4 to 15 established from the structural analysis of the polypeptide sequence of SEQ ID NO: 2 (Table 1).

TABLE 1

Amino acid sequence of the immunosuppressive polypeptides of this invention.

| SEQ ID NO: | Designation | Peptide sequence NH2-COOH |
|---|---|---|
| 4 | P1 | HisAspAsnAlaGlnLeuLeuThr |
| 5 | P2 | AlaIleAspLeuAlaAspAsnThrIleGlyIleAlaTyrThrGlyGly |
| 6 | P3 | GlnLeuLeuThrAlaIleAspLeu |
| 7 | P4 | AlaAspAsnThrIleGlyIleAla |
| 8 | P5 | IleGlyIleAlaTyrThrGlyGly |
| 9 | P6 | AsnAlaGlnLeuLeuThrAlaIleAsp |
| 10 | P7 | TyrThrGlyGlyMetCysTyrPro |
| 11 | P8 | LeuThrAlaIleAsp |
| 12 | P9 | AlaIleAspLeuAla |
| 13 | P10 | LeuThrAlaIleAspLeuAla |
| 14 | P11 | AlaIleAsp |

TABLE 1-continued

Amino acid sequence of the immunosuppressive
polypeptides of this invention.

| SEQ ID NO: | Designation | Peptide sequence NH2-COOH |
|---|---|---|
| 15 | P12 | LeuAsnArgIleSerHisAspAsnAla GlnLeuLeuThrAlaIleAspLeuAla AspAsnThrIleGlyIleAlaTyrThr GlyGly |

The polypeptide fragments of this invention do not necessarily have to be identical to the sequences outlined in SEQ ID NOs: 4 to 15, as long as they present the immunosuppressive function.

Thus, the invention's polypeptide fragments can be derived from SEQ ID NOs: 4 to 15 by deletion, substitution, addition or chemical modification of one or more amino acids. Fragments may comprise the amino acid conservative substitution based on the amino acid sequence of SEQ ID NOs: 4 to 15. In addition, fragments present at least 70% of the amino acid sequence identity with the SEQ ID NOs: 4 to 15. More preferably, fragments present 75%, 80%, 85%, 90%, 91%, 92%, 93%, 94%, 95%, 96%, 97%, 98% or 99% amino acid sequence identity with SEQ ID NOs: 4 to 15. Besides, a skilled in the art may determine the regions corresponding to the SEQ ID NOs: 4 to 15 in other polypeptides identical to the polypeptide in SEQ ID NOs: 2 or 3 of the invention.

From the identification and scheme of polypeptide sequences with a potentially immunosuppressive activity, the fragments of this invention are synthesized by well-known state of the art methods, such as chemical synthesis and recombinant DNA technology. The polypeptide chemical synthesis can be carried out in liquid or solid phases, according to Shin et al. review. (*J. Biochem. Molec. Biol.*, 38(5):517-525, 2005), typically using α-amino groups, α-carboxyl protection groups and/or functional groups of amino acids lateral chains.

Polypeptide fragments or its useful derivatives may also be obtained from polypeptide of SED ID NOs: 2 or 3 purified, produced by recombinant DNA, by methods that include digestion with enzymes, such as pepsin or papain. Alternatively, fragments comprised by this invention can be synthesized via an automatic peptide synthesizer, or be manually produced by well-known techniques (GEYSEN et al., 1978, *J. Immunol. Methods* 102: 259). Additionally, when synthesized by recombinant DNA technology, the site-directed mutagenesis can be used to prepare amino acid replacements in the invention's fragment sequence. This method is well known in the art and there are commercial kits available that facilitate its conduction.

The invention's polypeptides can also be covalently bonded to polyethylene glycol via amino groups or free carboxyl present in amino acids. Other derived fragments include glycosylated polypeptides or non-glycosylated polypeptides. Glycosylation can improve the half-life of circulating peptide fragments and allow modulation of immunosuppressive characteristics of derived fragments. Glycosylation can be biological or non-biological. For instance, biologically relevant N- or O-bonded carbohydrates are anticipated here. Other derived products, such as a succinate, are also covered.

Polypeptides in this invention can also exist as stereoisomers or stereoisomers mixtures; e.g., amino acids that comprise them can present configuration L-, D-, or be DL-racemic, regardless of each other. Therefore, it is possible to obtain isomeric mixtures, as well as racemic, or diastereomeric mixtures or pure diastereoisomers, depending on the number of asymmetric carbons and which isomers or isomeric mixtures are present. Thus, while the amino acid residues of the polypeptide sequences listed as SEQ ID NOs: 4 to 15 are all in L isomeric form, residues in D isomeric form can substitute any amino acids in the L form sequence, as long as this substitution preserves the immunosuppressive function of the invention's polypeptides. Substitution of L amino acids by D is known in the art and aims to protect this invention's polypeptides from proteolytic degradation. So, synthetic polypeptides in this invention are characterized by the fact the amino acid residues SEQ ID NOs: 4 to 15 are in L isomeric form or D isomeric form or DL racemic form.

Pharmaceutically acceptable salts can be used here, for example, mineral acids salts, such as hydrochlorides, hydrobromides, phosphates, sulfates, and the like; and organic salts, such as acetates, propionates, malonates, benzoates, and the like. Therefore, in one embodiment, the polypeptides of the invention can also be prepared and stored as salts. Many polypeptide salts can be formed or inter-modified by any known method. Cationic counter-ions that might be used in the compositions include, but are not limited to, ammonia ions, metallic ions, specially monovalent ions, divalent, or trivalent of alkali metals including sodium, potassium, lithium, cesium, earth alkaline metals including calcium, magnesium, barium, transition metals such as iron, magnesium, zinc, cadmium, molybdenum; other metals such as aluminum, and possible combinations between them.

Cationic counter-ions that might be used in the compositions include chloride, fluoride, acetate, trifluoroacetate, phosphate, sulfate, carbonate, citrate, ascorbate, sorbate, glutarate, ketoglutarate and possible combinations between them.

After chemical reaction, the polypeptides might be separated and purified by some known purification method. An example of such purification methods might include a combination of solvent extraction, distillation, column chromatography, recrystallization and similar.

Once the polypeptide of interest is similar to a snake venom protein (LHFII) containing undesirable properties for a developing drug such as, for example, hemorrhagic and proteolytic activity, it is of great importance to investigate whether the polypeptides of this invention present such properties.

The proteolytic effect is verified by spectrofluorometer using the FRET method (Fluorescence Resonance Energy Transfer) with fluorescence-quenching substrate, on which proteolytic activity with substrate hydrolysis is revealed by appearance of fluorescence. Another possibility would be the verification of hydrolysis capacity in known substrates. The proteolytic enzymes of viperidae venoms have, for example, the capacity to hydrolyze the fibrinogen and the C3 component of the human complement system, and verifying this effect is a way of inquiring about the proteolytic activity.

It is possible to determine the venom of *L. muta* and the polypeptides hemorrhagic activity using the Kondo et al method. (1960, Jpn. J. Med. Sci. Biol. 13: 43-52).

The polypeptides described in this invention are characterized by the absence of hemorrhagic and proteolytic effects.

In a further aspect of the invention, the immunosuppressive properties of the invention's polypeptides are verified, as well as it is assured that they do not present immunogenic potential, through experimental models of induced suppression and immunization, respectively.

For the invention's polypeptide immunosuppressive activity analysis, Lineage $H_{III}$ mice constitutively known as good responder to of antibody production are inoculated, intraperitoneally, and immunized with structurally complex and highly immunogenic antigens, such as sheep erythrocytes, a particulate antigen. The animals' serum is then analyzed regarding its hemagglutination activity: the lower is the hemagglutinating effect; the higher is the immunosuppressive capacity of the evaluated compound. The immunosuppressive activity can also be evaluated against a soluble antigen, such as human gamma globulin (HGG), adsorbed in aluminum hydroxide, and the antibodies titer determined by ELISA.

The immunogenicity is the capacity of a substance to induce an immune response. To evaluate the immunogenic potential of this invention's polypeptides, the antibody production is determined by the dosage of antibodies titer by ELISA after administration of the present invention polypeptides in potent adjuvants.

The invention's polypeptides of the present invention are not immunogenic, they do not induce generalized immunosuppression and are not toxic, nor do they interfere in any other physiological function in the organism, as verified by monitoring of the long survival of animals that received intraperitoneal polypeptides dosages, which is a great advantage over the immunosuppressive drugs widely used.

The invention's polypeptides act selectively and multi-specifically, diminishing antibodies production against antigens of several structure and nature, such as proteins, biologically active polypeptides, toxins, and bacterial or viral vaccines. They are effective against a first signal and present extended action. Even after a second administration of the same immunogen, the suppressive effect is maintained, resulting in reduction of the immune response, measured by antibody production.

This invention is also related to a method of producing a polypeptide in accordance to the invention with immunosuppressive activity comprising a nucleic acid insertion, an expression cassette or vector, according to the invention, in an in vivo expression system and the collection of the polypeptide produced by this system. Many in vivo expression systems, comprising the use of adequate host cells, are commercially available and the use of these systems is a well-known technique.

Particularly adequate expression systems include microorganisms, such as bacteria transformed with recombinant DNA expression vectors of bacteriophages, plasmid or cosmid; yeast transformed with yeast expression vectors; systems of insect cells infected with viral expression vectors (e.g., baculovirus); systems of plant cells transformed with viral expression vectors (e.g., cauliflower mosaic virus—CaMV; tobacco mosaic virus—TMV) or with bacterial expression vectors (e.g., Ti plasmid or pBR322); or animal cells systems. It is also possible to use translation systems cell free s to produce the invention's polypeptides.

The insertion of nucleic acid molecules codifying the invention's polypeptide into host cells can be performed by methods described in many common laboratory manuals, such as Davis et al., *Basic Methods in Molecular Biology* (1986) and Sambrook et al., *Molecular Cloning: A Laboratory Manual*, Cold Spring Harbor, N.Y. (1989).

The transformed or transfected host cell mentioned above is then grown in a suitable culture medium under conducive conditions that enables the expression of the invention's immunosuppressive polypeptides. The medium used to cultivate cells can be any suitable conventional culture medium to develop host cells, such as minimal or complex media containing appropriate supplements. The suitable media are available from commercial suppliers or can be prepared following published recipes (for example, in the American Type Culture Collection catalog). The polypeptides produced by the cells can be later recovered from the cell or culture medium by conventional procedures, including separation of host cells from the medium by centrifugation or filtration, precipitation of protein aqueous components from the supernatant or filtrate with a salt, for example, ammonia sulfate, purified by multiple chromatographic procedures, such as ionic exchange chromatography, exclusion chromatography, hydrophobic interaction chromatography, gel filtration chromatography, affinity chromatography or similar, depending on the type of polypeptide.

According to the invention's additional aspect, a method for producing a polypeptide with immunosuppressive activity is provided, which comprises:

(a) transfer an invention's polynucleotide to a host cell to obtain a transformed or transfected host cell;

(b) culturing of the transformed or transfected host cell to obtain a culture of cells;

(c) expression of the invention's polynucleotide in a transformed or transfected host cell to produce a polypeptide; and (d) isolation the invention's polypeptide from the cell or from the cell culture.

In one particularly embodiment, the host cell is a prokaryotic microorganism or an eukaryotic cell or microorganism.

As a particular aspect, the said polypeptide is provided with a tag.

In another aspect, a pharmaceutical composition is provided, comprising at least one polypeptide with immunosuppressive activity according to the invention, or its pharmaceutically acceptable salts or derivatives, and at least one carrier or pharmaceutically acceptable excipient. Preferably, one or more polypeptides comprising the amino acid sequence of SEQ ID NOs: 2-15, or that presents at least 70% identity to SEQ ID NOs: 2-15. The polypeptide could be a derivative, as mentioned above, or comprise a fused tag on its amino end or carboxyl terminal.

The pharmaceutically acceptable carriers or excipients are selected based on the invention's final composition presentation, that might be as a capsule, tablet, orally or nasally administrated solution, injectable solution for intramuscular, intravenous, cutaneous or subcutaneous administration. Pharmaceutically acceptable excipients, carriers or stabilizers do not show toxicity to the recipient organism in the dosages and concentrations used, and include buffers such as phosphate, citrate, and other organic acids; antioxidants such as ascorbic acid and methionine; preservatives such as octadecyldimethylbenzyl ammonium chloride, hexamethonium chloride, benzalkonium chloride, benzethonium chloride, phenol, butyl alcohol, benzyl alcohol, alkyl parabens like methyl-e propyl paraben, catechol, resorcinol, cyclohexanol, 3-pentanol and m-cresol; proteins such as albumin, gelatin and immunoglobulin; amino acids, monosaccharides, disaccharides, and other carbohydrates like glucose, mannose, sucrose, mannitol, or sorbitol; polymeric excipients such as polyvinylpyrrolidones, Ficoll®, dextrins and polyethylene glycols; flavoring agents, sweeteners, antistatic agents, chelating agents such as EDTA or EGTA; ion releasing salts like sodium, metal complexes, non-ionic surfactants such as polysorbates 20 and 80; lipids like phospholipids, fatty acids and steroids, such as cholesterol.

Methods for preparation of multiple pharmaceutical compositions are well known or will be apparent in light of this invention by an expert in pharmaceutical technology.

Besides, the compositions might comprise additives for the purpose of increasing administration and storage capacity, resistance to degradation, bioavailability, half-life, to provide isotonic preparations etc. Common additives for pharmaceutical preparations are well known.

Moreover, the invention's polypeptides can be used in combination with other therapeutic agents, such as corticosteroids, glucocorticoids, cytostatic agents, cytotoxic agents, monoclonal antibodies, recombinant polypeptides, antibodies and nucleoside analogs. Non-limiting examples of therapeutic agents mentioned above are: leflunomide, mycophenolate mofetil, chlorambucil, cyclophosphamide, cladribine, fludarabine, azathioprine, methotrexate, cyclosporine, tacrolimus, prednisone, cortisone, hydrocortisone, thalidomide and sirolimus.

Pharmaceutical compositions must comprise a therapeutically effective quantity of polypeptide or its pharmaceutically acceptable salts or derivatives. For any compound, the therapeutically effective dosage can be initially estimated, either in cell culture assays, such as neoplastic cells, or in animal models, usually mice, rabbits, dogs, and pigs. The animal model can also be used to determine the suitable concentration range and administration route. This kind of information can be used later to determine the dosage and administration route in humans.

The pharmaceutical composition according to this invention comprises from 0.1% to 99% w/w, preferably 1% to 60% w/w, particularly 10% to 50% w/w of the polypeptides or its pharmaceutically acceptable salts or derivatives.

According to this invention, the administration route of these pharmaceutical compositions can be, but is not limited to sublingual, nasal, intravenous, intramuscular, intraperitoneal, intra-articular, subcutaneous, cutaneous, transdermal and, preferably, oral.

In a further aspect of the present invention, polypeptides, or pharmaceutically acceptable salts or derivatives thereof, are provided for prevention or treatment of conditions that need immunosuppression. Preferably, the polypeptide comprises any of the SEQ ID NOs: 2-15, or that presents at least 70% identity to SEQ ID NOs: 2-15, or its pharmaceutically acceptable salts and derivatives. The conditions that need immunosuppression can be selected from the group consisting of inflammatory, autoimmune, allergic, and infectious diseases, and rejection to transplanted organs.

The invention also refers to the use of polypeptides, or pharmaceutically acceptable salts or derivatives thereof, for the manufacture of a medicament for the prevention or treatment conditions that require immunosuppression. Preferably, the polypeptide comprises any of the SEQ ID NOs: 2-15, or that presents at least 70% identity to SEQ ID NOs: 2-15, or pharmaceutically acceptable salts and derivatives thereof.

In another aspect, the invention provides a method for prevention or treatment of conditions that require immunosuppression, characterized by comprising the administration to an individual in need of such treatment, a therapeutically effective amount of a polypeptide according to the invention, or pharmaceutically acceptable salts or derivatives thereof. Preferably, the polypeptide comprises any of the SEQ ID NOs: 2-15, or that presents at least 70% identity to SEQ ID NOs: 2-15, or pharmaceutically acceptable salts and derivatives thereof.

Preferably, this individual is a human being in need of suppression of the immune response.

The conditions that need immunosuppression are selected from the group consisting of inflammatory, autoimmune, allergic, and infectious diseases and rejection to transplanted organs.

For this invention, inflammatory diseases can be selected from the group consisting of idiopathic, chronic and acute inflammatory diseases. Autoimmune diseases include diseases caused by decreased immune tolerance to components of the organism itself, due to an alteration on the differentiation process between self and external antigens, and can be selected from the group of chronic rheumatoid arthritis, juvenile rheumatoid arthritis, systemic erythematosus lupus, scleroderma, Crohn's disease, mixed connective tissue disease, dermatomyositis, Sjögren's syndrome, Bechet's disease, multiple sclerosis, primary myxoedema, Hashimoto's disease, psoriasis, pernicious anemia, idiopathic thrombocytopenic purpura, vasculitis, heparin-induced thrombocytopenia, uveitis, hemolytic anemia, thrombocytopenic purpura, pemphigus vulgaris, vasculitis caused by antineutrophil cytoplasmic antibodies, Goodpasture's syndrome, acute rheumatic fever, myasthenia gravis, hyperthyroidism, insulin resistant diabetes, polyarteritis nodosa, post-streptococcal glomerulonephritis, sepsis and serum sickness. The allergic diseases can be defined as immunological hypersensitivity reactions mediated by antibodies, immune complexes (formed due to complement system activation) or cells against foreign antigen (allergen), manifested by tissue inflammation or organ dysfunction, and can be selected from a group of atopic dermatitis, asthma, bronchitis, rhinitis, hay fever, urticaria, angioedema, contact dermatitis, allergic gastroenteropathy, anaphylaxis, hemolytic anemia or hemolytic disease of the newborn, sinusitis, rheumatic fever hypersensitive pneumonitis, streptococcal glomerulonephritis and allergic alveolitis.

The exact effective quantity to a human being depends on the disease's severity state, the individual's overall health status, age, weight, sex, diet, administration time and frequency, drug combination(s), reaction sensitivities and tolerance/response to therapy. This way, the dosage depends on a number of factors that cannot be measured before the study of clinical tests. However, the technician is capable of achieving suitable dosages for different treatments.

The examples below are merely illustrative. They must be applied solely for a better understanding of the developments in this invention and are not to be used with the intention to limit the described objects.

Example 1. Obtaining the Inhibitory Factor of Humoral Immune Response to Heterologous Antigens of *Lachesis muta*

The *L. muta* venom, supplied by the Production Division of Butantan Institute, Laboratory for Hyperimmune Plasma Processing, was initially subjected to molecular exclusion chromatography according to Stephano et al. (BRPI0502080-8, 2005). The F4 fraction was dialyzed, lyophilized, resuspended in Tris-HCl buffer and subjected to molecular exclusion column chromatography (SUPEROSE® 12) in 20 mM Tris-HCl buffer, pH 7.4, under a 24 mL/hour flow. The F2 fraction obtained (peak 2) (FIG. 1) was then subject to reverse phase chromatography, using a Wide-Pore Butyl C18 column, in HPLC system. The fractions were eluted under 1.0 mL/min constant flow in acetonitrile linear gradient and 0.1% trifluoroacetic acid (FIG. 2).

Peak 7 (FIG. 2) represents the humoral immune response inhibitory factor to heterologous antigens, immediately vacuum dried for acetonitrile removal and stored at −20° C. All purification steps were monitored in $Abs_{280nm}$.

Example 2. Characterization of Humoral Immune Response Inhibitory Factor to Heterologous Antigens of *L. muta*

Electrophoretic analysis in SDS-PAGE gel (12.5%), performed in reducing conditions and stained with silver, demonstrated the purity and approximated molecular mass of 23 kDa of the humoral immune response inhibitory factor to purified heterologous antigens (FIG. 3, samples A, B and C with increasing protein concentration, 1, 2 and 3 µg, respectively).

The protein factor was analyzed by mass spectrometry, by peptide mass fingerprinting technique, presenting substantial similarities to the snake venom metalloproteinase (SVMP), the mutalysine-II, also called *Lachesis muta* Hemorrhagic Factor (LHF-II, Access No. P22796).

The metalloproteinase LHF-II, SVMP class P-I, is a zinc dependent endopeptidase with hemorrhagic effect and high proteolytic activity, with 200 amino acids, molecular weight of 22.5 kDa and 6.6 isoelectric point (FOX J W & SERRANO S M, 2005. *Toxicon* 8:969-85).

The SVMPs, classified according to their structural domain (P-I, P-II, P-III and P-IV), are in the reprolysin group and have mass between 20 and 100 kDa. The "HEXXH" consensus sequence, where X represents any amino acid residue, is common and corresponds to a metal ion binding motif (usually zinc), coordinated by histidine and glutamic acid residues, essential for the catalysis mechanism. They act directly on extracellular matrix components and are considered the main factors involved in hemorrhage (FOX J W & SERRANO S M, 2005. *Toxicon* 8:969-85).

FIG. 4 presents the complete sequence of amino acids of the LHF-II and highlights the peptide sequence of the purified factor identical to LHF-II.

Example 3. Cloning of cDNA that Codifies the Invention's Immunosuppressive Recombinant Polypeptides (SEQ ID NOs: 2 and 3)

The total RNA of *L. muta* venom gland was isolated by extraction with TRIZOL® reagent (Gibco-BRL Life Technologies; according to manufacturer's instructions) for the synthesis of complementary DNA (cDNA) using the cDNA CYCLE™ kit (Invitrogen, USA; according to manufacturer's instructions).

For the reaction, 5 µg of total RNA and 1 µg of random primers were used, the sample was subjected to denaturation pretreatment at 65° C. for 10 min, followed by 2 min at room temperature. Were added 10 U of RNase inhibitor, 4 µL of buffer for Reverse Transcriptase (5×), 100 mM of dNTPs, 80 mM of sodium pyrophosphate, 11.5 µL of sterile distilled deionized water treated with DEPC (diethyl-pyrocarbonate) and 5 U of Reverse Transcriptase enzyme—AMV-RT, and incubated for 1 hour at 42° C.

The cDNA obtained was then submitted to two PCR sequencing reactions with degenerated primers (SEQ ID NOs: 16 and 17), designed from the conserved amino- and carboxy-terminal regions from the sequence obtained by Peptide Mass Fingerprinting Analysis (FIG. 4).

The amplification resulted in two fragments, one of 300 pairs of bases (pb) and another of 600 pb, approximately (FIG. 5; (A) negative control; (B) first PCR reaction product; (C) second PCR reaction product, using the product obtained by the first PCR reaction as a template).

The biggest fragment obtained was purified according to Ausubel et al. (1995) and bonded to the PGEM® T easy plasmid (Promega) according the manufacturer's instructions.

The bonded products (recombinant plasmid DNA) were transformed in competent *Escherichia coli* XL1 Blue cells and 100 positive clones were selected using IPTG/X-GAL. After the selected clones multiplication, the recombinant plasmid DNA of each clone was isolated and subjected to enzyme restriction analysis with EcoR-I endonuclease to confirm the presence of the gene fragment of interest (FIG. 6. 1—Molecular weight standard-lambda phage DNA digested with Hind III; 2 to 20—clones digested with restriction enzyme EcoR-I).

The clones with inserts higher or equal to 500 pb (24 of the 100 selected clones) were subjected to DNA sequencing reactions (Big Dye kit, Applied Biosystems, USA; DNA sequencer, capillary electrophoresis model ABI PRISM™ 3100, Applied Biosystems, USA; according the manufacturer's instructions). The primers used for sequencing were T7 (SEQ ID NOs: 20, 5' taatacgactcactataggg 3') and SP6 (SEQ ID NOs: 21, 5' ttctatagtgtcacctaaat 3'), complementary to pGEM-T vector sequence that flanks the multiple cloning region, sense and antisense, respectively. The sequencing result was used as a template to design specific primers containing the Xho-I restriction site (SEQ ID NO: 18) and Nco-I (SEQ ID NO: 19) for the directed subcloning of the sequence of interest in the vector pRSET-A (Invitrogen, USA). FIG. 7 presents the sequence obtained through DNA sequencing analysis and position and sequence of primers used for complementary DNA subcloning (SEQ ID NO: 1) that codifies the recombinant polypeptide of SEQ ID NO: 2.

The DNA fragment of interest was amplified by PCR using specific primers mentioned above (SEQ ID NOs: 18 and 19) and as a template, the clone whose gene sequencing result gave rise to the sequence represented on FIG. 7 (SEQ ID NO: 1). The amplified products were again inserted into the pGEM-T vector and into competent prokaryotic host cells (*E. coli*) for storage and amplification. Afterwards, the pGEM-T vector containing the DNA fragment and the expression vector pRSET-A were cleaved with endonucleases Xho-I and Nco-I. The DNA fragment and the cleaved expression vector were subjected to a linking reaction with T4 ligase enzyme. The products were transformed into competent *Escherichia coli* XL1 Blue cells and selected by the IPTG/X-gal system for extraction of plasmid DNA. The restriction analysis was then performed with NcoI and Xh enzymes used in the subcloning to confirm the correct insert dimension and orientation.

The final construction comprised the pRSET-A vector and the complementary DNA SEQ ID NO: 1, codifying a recombinant polypeptide of SEQ ID NO: 3.

Example 4. Similarity Analysis of SEQ ID NOs: 1 and 2

The sequence SEQ ID NO: 1 was subject to similarity analysis using BLAST (Basic Local Alignment Search Tool), available at the National Center for Biotechnology Information (NCBI) website nlm.nih.gov. The sequence SEQ ID NO: 1 was translated by the TRANSLATE TOOL at the website expasy.ch; and manually analyzed using BioEdit (HALL, T. A. 1999, *Nucl. Acids. Symp. Ser.*, 41:95-98). The BLOSUM 62 matrix (Blocks Substitution Matrix) was used (HENIKOFF & HENIKOFF. 1992, *PNAS*, 89:10915-10919). The deduced amino acid sequence SEQ ID NO: 2 was submitted to analysis at the Conserved Domains Database (CDD) for determination of possible conserved domains (MARCHLER-BAUER et al., 2005, *Nucleic Acids Res.* 33:D192-6). Through the rpsBlast tool, a multiple alignment was performed between the recombinant polypeptide deduced sequence and other polypeptide sequences present in the collection, already divided in families and respective bio functions.

The alignment result in the CDD protein bank revealed the recombinant polypeptide producing clone sequence of SEQ ID NO: 2 presents amino acid regions common to other reprolysin (M12B). FIG. 8 illustrates the amino acid deduced sequence alignment SEQ ID NO: 2 with the consensus sequence of 9 representatives of the protein database alignment, whose identity vary from 57 to 81%, but with the catalytic motif conserved in all of them. It shows the "HEXXH" catalytic motif present in all members of the metalloproteinases family, and "X" represents any amino acid. It is important to highlight that one of the common features of the reprolysin family is the proteolytic activity and, in some cases, such as LHFII and Fibrolase, also present hemorrhagic effects. However, as demonstrated on example 8, despite similarities to metalloproteinase family, the recombinant polypeptides of this invention, surprisingly, do not present such proteolytic nor hemorrhagic effect.

Example 5. Expression of the Recombinant Immunosuppressive Polypeptide (SEQ ID NO: 3)

The final construction presenting the expression vector (pRSET-A) and the cDNA sequence obtained from the *L. muta* RNA (SEQ ID NO: 1) was initially transformed into competent *E. coli* BL21 (DE3) cells (Invitrogen) and later into competent ORIGAMI™ (DE3) pLysS cells (Novagen).

The recombinant polypeptide produced from the final construction presented, in addition to the amino acid sequence SEQ ID NO: 2, six histidine residues, the portion derived from protein 10 of T7 phage and a enterokinase cleavage site (7.87 kDa), resulting in a polypeptide with molecular mass of approximately 30 kDa (SEQ ID NO: 3).

The soluble recombinant polypeptide was obtained only after expression protocols optimization using the Origami (DE3) pLysS bacterial strain with 1 mM IPTG induction for 72 hours at 20° C.; mild agitation and Tris-HCl 48 mM lysis buffer, SDS 70 mM, pH 6.8.

Example 6. Purification and Biochemical Characterization of the Recombinant Polypeptide (SEQ ID NO: 3)

Bacterial lysate supernatant samples, where the recombinant polypeptide expression was induced, were submitted to affinity chromatography in $Ni^{++}$ column coupled to sepharose, eluting the recombinant polypeptide and then subjecting it to SDS-PAGE analysis. FIG. 9 shows the eletrophoresis result (SDS PAGE—12.5% gel, reducing conditions and silver staining) of samples collected during the affinity chromatography for recombinant polypeptide purification showing the presence of two bands, both corresponding to the produced recombinant polypeptide (FIG. 9—amount per sample—20 μg; Caption: (A) Eluate; (B) Equilibration buffer (0.002 M $Na_3PO_4$, 0.5 M NaCl, pH 7.8); (C) wash buffer (0.002 M $Na_3PO_4$, 0.5 M NaCl, pH 6.0); (D) Wash Buffer with 30 mM imidazole; (E) Wash Buffer with 60 mM imidazole; (F) Wash buffer with 400 mM imidazole).

A sample containing 60 μg of the produced recombinant polypeptide was subject to isoelectric focusing in linear gradient with pH varying from 3 to 10, and the second dimension performed in 12.5% SDS-PAGE; the gel was stained with silver, showing a polypeptide with molecular mass of approximately 30 kDa and IEP 6.2 (FIG. 10). The yield of recombinant polypeptide expression was about 2 mg/L.

Example 7. Theoretical Modeling of the Immunosuppressive Recombinant Polypeptide (SEQ ID NO: 2) and Design of Polypeptide Fragments (SEQ ID NOs: 4 to 15)

From the deduced sequence analysis of the recombinant polypeptide obtained, theoretical models of the polypeptide's secondary (FIG. 11) and tertiary structure (FIG. 12) were created to identify the regions with higher probability of involvement in the immunosuppressive activity.

The secondary structure prediction was done with PSIPRED (Position Specific Iterated Prediction) (JONES, 1999, *J Mol. Biol.,* 292:195-202) and GOR4 (Secondary structure prediction) (GARNIER et al., 1990, *Biochem Soc. Symp.,* 57:11-24) tools, which compare the target amino acid sequences with the database of secondary structures established experimentally (FIG. 11).

The data obtained by circular dichroism for the recombinant polypeptide shows that the secondary structure elements (Table 2) are in accordance with the theoretical model predicted by the computer tools mentioned above.

TABLE 2

Determination of secondary structures.

| | α-helix | β leaves | Connections |
|---|---|---|---|
| Theoretical model | 29.5% | 24.5% | 46% |
| Recombinant Polypeptides | 28.1% | 23.3% | 55% |

The circular dichroism analysis was performed in JASCO 810 spectropolarimeter coupled with a Peltier temperature control system, in wave lengths between 190 e 260 nm, 100 mdeg sensitivity, 0.2 nm resolution, 8 seconds response time at 200 nm/min speed. The secondary structural elements estimated was obtained using the CDNN protein deconvolution tool (SREERAMA, N. & WOODY R. W. (1993) *A self consistent method for the analysis of protein secondary structure from circular dichroism. Anal. Biochemistry*, p. 209).

The physiochemical parameters of the polypeptide-deduced sequence were calculated using the ProtParam Tool (GASTEIGER et al., 2005. *Hatfeld: Humana Press*, p. 571-607).

The tridimensional models of the recombinant polypeptide were constructed through comparative modeling from the search for proteins whose secondary structure were similar to the predicted secondary structure using the SWISS-MODEL, ESyPred3D and SDSC1 tools.

The constructed tridimensional model quality was assessed with the following tools: VERIFY 3D (LUTHY et al., 1992, *Nature,* 356: 83-5), *WHATIF* (VRIEND, 1990, *J. Mol. Graph.,* 8:52-6; HOOFT et al., 1996. *Proteins,* 26: 363-76) and PROCHECK (LASKOWSKI et al., 1998, *Curr. Opin. Struct. Biol.,* 8:631-9). The parameters tested in these programs were the bonds lengths and angles, peptide bonds' planes and side chains' rings, chirality, main and side chains' torsion angles, in addition to steric hindrance between pairs of unrelated atoms; and VERIFY 3D and WHATIF programs perform, with high resolution, comparisons between the models obtained and the resolved proteins.

The built and validated structural model for the recombinant polypeptide is shown in FIG. 12, where cylinders represent a helices and arrows represent β sheets, while loops are represented by a solid line.

It is observed that the catalytic motif is found in a binding pocket at the end of the carboxy-terminal, involving an alpha helix and a connection (amino acids 130-195). The predictive analysis identify in this region of the polypeptide, the existence of disulfide bonds between cysteines 157-162, 155-179 and 115-195 (FIG. 12), probably involved in maintaining the three-dimensional structure responsible for the formation of the binding pocket containing the motif "HEXXH" observed.

The polypeptide's amino-terminal region (amino acid 1 to 84) has few connection regions (loops), sites likely to be more exposed on the surface of the polypeptide, and more likely to be related to the immunosuppressive activity described.

Based on this structural information, the region of the recombinant polypeptide chosen for the synthesis of polypeptide fragments occur from amino acid 85 to amino acid 113, and has a more favorable location in the predicted three-dimensional structure due to the existence of a larger number of connections and to the absence of alpha-helix structures and catalytic domains already described. Thus, all synthesized polypeptide fragments are found in this region (SEQ ID NOs: 4 to 15).

Example 8: Analysis of Proteolytic Activity and the Hemorrhagic Potential of the Recombinant Polypeptide (SEQ ID NO: 3)

The possible proteolytic activity of the recombinant polypeptide was evaluated in spectrofluorometer using extinguished fluorescence substrate (FRET)-Abz-FRSSRQ EDDnp, sensitive to hydrolysis by serine and metalloproteinases. As negative control, PBS buffer was used.

The absence of recombinant polypeptide proteolytic activity on the FRET substrate is noticed, even using 10 μg of polypeptide and monitoring the fluorescence for 1 hour.

To confirm the absence of enzymatic activity, one experiment was carried out a fibrinogenolytic assay. Samples containing 30 μg human fibrinogen were incubated with 5 μg of purified recombinant polypeptide at 37° C. for 5 hours. According to the caption on FIG. 13: (A) Fibrinogen; (B) Fibrinogen+venom; (C) Fibrinogen+recombinant polypeptide. The samples were subjected to SDS-PAGE (10%) analysis under reducing conditions and the gel was stained with Coomassie blue. FIG. 13 shows that the recombinant polypeptide was not able to hydrolyze fibrinogen. However, the positive control used—whole *L. muta* venom—caused a noticeable degradation of fibrinogen.

Other substrate tested for possible proteolytic activity of the recombinant polypeptide was the C3 component of human complement system. Samples containing 9 μg of purified human C3 component were incubated with 5 μg of purified recombinant polypeptide at 37° C. for 5 hours. According to the caption on FIG. 14: (A) Human C3; (B) Human C3+venom; (C) Human C3+polypeptide. The samples were subjected to SDS-PAGE (10%) analysis under reducing conditions and the gel was stained with Coomassie blue. FIG. 14 shows that the recombinant polypeptide was unable to cleave the C3 component.

The hemorrhagic activity of the recombinant polypeptide was evaluated according to the method described by Kondo et al. (1960. *Jpn. J. Med. Sci. Biol.,* 13:43-52). Groups (5 animals/groups) of BALB/c (18-22 g) mice received an intradermal injection with 4 mg of *L. muta* venom or 50 mg recombinant polypeptide; the group used as negative control received only phosphate saline buffer (PBS). After 2 hours, the animals were euthanized and the skin removed to assess the presence of hemorrhage. FIG. 15 shows hemorrhagic activity of *L. muta* venom (panel B) compared to the non-inoculated control animals (panel A) and the recombinant polypeptide (panel C), which shows no hemorrhagic activity, even at a concentration 12.5 times higher than that of crude venom.

Example 9: Immunogenicity Analysis

Anti-recombinant polypeptide antibodies were measured by ELISA. Samples containing the recombinant polypeptide (SEQ ID NO: 3) were used to sensitize ELISA plates (1 μg/well) which were incubated with increasing dilutions of sera of animals immunized with the recombinant polypeptide (SEQ ID NO: 3). The reactions were developed by the addition of anti-mice-IgG conjugated to peroxidase (1: 7,500), followed by addition of OPD (o-Phenylenediamine dihydrochloride) and $H_2O_2$. The reading of the reactions was performed at λ492 nm on a plate spectrophotometer. The titer was established as the highest dilution of experimental sera which optical densities were three times higher than those obtained for normal serum at the same dilution. The data correspond to values obtained from two independent experiments. The significance between different groups (6 animals/group) was $p<0.01$.

The results demonstrated that the recombinant polypeptide has very low or no immunogenic potential, since it was not able to induce the production of specific antibodies.

The polypeptide P6 (SEQ ID NO: 9) also did not show immunogenicity, and is unable to induce the production of antibodies (ELISA performed as described above, the polypeptide of SEQ ID NO: 9 used to sensitize the plaque and to immunize the animals).

The immunization protocol used in the experiments described above was: groups of mice with good response to antibody production, Lineage $H_{III}$ mice (6 animals/group) were injected, intraperitoneally, with polypeptide P6 (3 mg) or recombinant polypeptide SEQ ID NO: 3 (50 μg). One group was used as a positive control, receiving human gamma globulin (HGG). Bleeding was performed seven days after immunization and antibody production was assessed by ELISA. The values obtained for the treatment with the recombinant polypeptide SEQ ID NO: 3 and P6 polypeptide were significantly different (Student t parametric test—$p<0.001$) to those got from animals immunized with HGG.

Example 10: Immunosuppressive Activity Analysis

To evaluate immunosuppressive activity of the recombinant polypeptide, groups of Lineage $H_{III}$ mice (6 animals/group) were inoculated or not with 50 μg of the recombinant polypeptide (SEQ ID NO: 3) intraperitoneally 72 hours before immunization with sheep erythrocytes ($E^S$) at a concentration of 1×10 cells/animal (range in which the immunosuppressant effect was stronger). An untreated group was used as positive control and received only $E^S$. Samples of 50 μL $E^S$ (2% v/v) were incubated with 50 μL of the sera from immunized animals (serially diluted) in 96

U-bottom well plates for 8 hours at room temperature. As negative control, E^S were incubated with PBS only. Antibody titers were that ones whose higher serum dilutions promoted agglutination of erythrocytes. The data are representative of three independent experiments. The significance between different groups was $p<0.01$ (FIG. 16).

Serum from animals treated only once or not treated with immunosuppressive recombinant polypeptide was used to evaluate the antibody response. FIG. 16 clearly shows that serum from animals that were previously inoculated with the recombinant polypeptide, as well as the negative control, were unable to promote hemagglutination, unlike the serum of untreated animals inoculated with E^S, which showed high hemagglutinating capacity, thus proving immunosuppressive activity of the recombinant polypeptides of this invention.

The immunosuppressive activity of the recombinant polypeptide was also tested for soluble antigens. Groups of $H_{III}$ mice (6 animals/group) were treated intraperitoneally with 50 μg of the recombinant polypeptide (SEQ ID NO: 3) and after 0, 24 or 72 hours, immunized intraperitoneally with human gamma globulin (HGG) adsorbed on Al(OH)$_3$ (10 μg/animal); the untreated group was used as a positive control receiving only HGG. Titers were determined by ELISA and calculated considering the highest dilution of experimental sera whose O.D. (optical density) was five times higher than those obtained for normal serum at the same dilution. The significance between the two groups was $p<0.05$ (FIG. 17).

The results showed that suppression of anti-HGG antibody production was induced in a prophylactic and antigen-specific manner until 24 hours after the treatment with the purified recombinant polypeptide (FIG. 17).

The chemically synthesized polypeptide fragments were also tested for possible immunosuppressant action.

The evaluation of the immunosuppressive activity was tested using the $H_{III}$ mice (6 animals/group) inoculated with the polypeptide named P6 (SEQ ID NO: 9; 3 μg/animal) or recombinant polypeptide of SEQ ID NO: 3 (50 μg/animal) and after 24 hours, with further inoculation of human gamma globulin (HGG) in Al(OH)$_3$. FIG. 18 shows the inhibition of anti-HGG antibody production promoted by P6, as observed for the recombinant polypeptide (SEQ ID NO: 3).

The immunosuppressive activity of the synthetic polypeptide P2 (SEQ ID NO: 5) and P6 (SEQ ID NO: 9) was evaluated against HGG, taking into account immunosuppression time after preventive treatment and antigen inoculation. In all protocols, animals received a single dose of the tested polypeptides. In this experiment, the $H_{III}$ mice (5 animals/group) were treated intraperitoneally with 3 μg of P6 or 3 μg of P2, and after 24 hours, were immunized intraperitoneally with HGG adsorbed on Al(OH)$_3$ (10 μg/animal); The untreated group was used as a positive control receiving only HGG. Another positive control was a group who received a 3 μg dose of the polypeptide, whose sequence "NH2-SerAnsGlnAspLeuIleAnsValGlnSerArgArgArgAsp-COOH" (SEQ ID NO: 22), does not represent the polypeptides claimed in this invention and, after 24 hours, were immunized intraperitoneally with HGG adsorbed on Al(OH)$_3$ (10 μg/animal). The negative control was represented by a group called normal serum, i.e., serum from untreated and non-immunized animals. O.D. values obtained from the 1:500 dilution were presented herein as average+ standard deviation and were statistically analyzed by Student t test. Values were considered significant when $p<0.0001$ (*); $p<0.005$ (); $p<0.05$ (*) compared to the positive control, i.e., animals immunized only with HGG. Thus, the $H_{III}$ mice groups received polypeptides SEQ ID NO: 22, P2 and P6. The results show that after 7, 13 and 36 days the suppression of anti-HGG antibody production was induced after treatment with P2 and P6 (FIG. 19).

The invention claimed is:

1. A polypeptide, or a pharmaceutically acceptable salt thereof, wherein the polypeptide comprises the amino acid sequence of

SEQ ID NO: 2 or SEQ ID NO: 3.

2. A pharmaceutical composition comprising a polypeptide as defined in claim 1, or a pharmaceutically acceptable salt thereof, and a pharmaceutically acceptable carrier or excipient.

3. A pharmaceutical composition comprising a polypeptide as defined in claim 1, or a pharmaceutically acceptable salt thereof, and a pharmaceutically acceptable carrier or excipient, wherein the pharmaceutical composition further comprises an additional therapeutic agent.

4. A method for producing a polypeptide, comprising:
(a) providing a host cell comprising an expression cassette which comprises a polynucleotide encoding the polypeptide of claim 1 operably linked to a promoter and a transcription terminator;
(b) cultivating said cell under conditions conducive to polypeptide production; and
(c) isolating said polypeptide from cell or culture media surrounding said cell.

5. A method for producing a polypeptide, comprising:
(a) providing a host cell comprising an expression cassette which comprises a polynucleotide encoding the polypeptide of claim 1 operably linked to a promoter and a transcription terminator;
(b) cultivating said cell under conditions conducive to polypeptide production; and
(c) isolating said polypeptide from cell or culture media surrounding said cell, wherein said polypeptide further comprises a tag.

* * * * *

SEQUENCE LISTING

<160> NUMBER OF SEQ ID NOS: 31

<210> SEQ ID NO 1
<211> LENGTH: 600
<212> TYPE: DNA
<213> ORGANISM: Artificial Sequence
<220> FEATURE:
<223> OTHER INFORMATION: Lachesis muta cDNA

<400> SEQUENCE: 1

```
ttctcacaga aatacattga acttgttgta gttgcagatc acggaatgtt cacgaaatac      60
aatggcaatt taaatactat aagaacacgg gtacatgaaa ttgtcaacac tctaaatggg     120
ttttacagat ctttgaatat tcatatctca ctgactgacc tagaaatttg gtccaaccaa     180
gatttgatca acgtgcagtc agcagcggct gatactttga aaacatttgg agagtggaga     240
gagagagtct tgctgaatcg cataagtcat gataatgctc agttactcac ggccattgac     300
cttgctgata atactatagg aatagcttac acaggcggca tgtgctaccc gaagaattct     360
gtaggaattg ttcaggatca tagtccaaaa actcttttga ttgcagttac aatggcccat     420
gagctgggtc ataatctggg catgaagcat gatgaaaatc attgtcattg cagtgcttcc     480
ttctgcatta tgcctcccag tttaagtgaa ggaccttcct atgagttcag cgattgtagt     540
aaggattatt atgagatgtt tcttactaag cgaaagccac aatgcatcct gaacaagcca     600
```

```
<210> SEQ ID NO 2
<211> LENGTH: 200
<212> TYPE: PRT
<213> ORGANISM: Artificial Sequence
<220> FEATURE:
<223> OTHER INFORMATION: Recombinant polypeptide

<400> SEQUENCE: 2

Phe Ser Gln Lys Tyr Ile Glu Leu Val Val Ala Asp His Gly Met
1               5                   10                  15

Phe Thr Lys Tyr Asn Gly Asn Leu Asn Thr Ile Arg Thr Arg Val His
                20                  25                  30

Glu Ile Val Asn Thr Leu Asn Gly Phe Tyr Arg Ser Leu Asn Ile His
            35                  40                  45

Ile Ser Leu Thr Asp Leu Glu Ile Trp Ser Asn Gln Asp Leu Ile Asn
50                  55                  60

Val Gln Ser Ala Ala Ala Asp Thr Leu Lys Thr Phe Gly Glu Trp Arg
65                  70                  75                  80

Glu Arg Val Leu Leu Asn Arg Ile Ser His Asp Asn Ala Gln Leu Leu
                85                  90                  95

Thr Ala Ile Asp Leu Ala Asp Asn Thr Ile Gly Ile Ala Tyr Thr Gly
            100                 105                 110

Gly Met Cys Tyr Pro Lys Asn Ser Val Gly Ile Val Gln Asp His Ser
        115                 120                 125

Pro Lys Thr Leu Leu Ile Ala Val Thr Met Ala His Glu Leu Gly His
    130                 135                 140

Asn Leu Gly Met Lys His Asp Glu Asn His Cys His Cys Ser Ala Ser
145                 150                 155                 160

Phe Cys Ile Met Pro Pro Ser Leu Ser Glu Gly Pro Ser Tyr Glu Phe
                165                 170                 175

Ser Asp Cys Ser Lys Asp Tyr Tyr Glu Met Phe Leu Thr Lys Arg Lys
            180                 185                 190

Pro Gln Cys Ile Leu Asn Lys Pro
        195                 200

<210> SEQ ID NO 3
<211> LENGTH: 267
<212> TYPE: PRT
<213> ORGANISM: Artificial Sequence
<220> FEATURE:
<223> OTHER INFORMATION: Recombinant polypeptide

<400> SEQUENCE: 3

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Glu Leu Phe Ser Gln Lys Tyr Ile Glu Leu Val Val
            35                  40                  45

Val Ala Asp His Gly Met Phe Thr Lys Tyr Asn Gly Asn Leu Asn Thr
50                  55                  60

Ile Arg Thr Arg Val His Glu Ile Val Asn Thr Leu Asn Gly Phe Tyr
65                  70                  75                  80

Arg Ser Leu Asn Ile His Ile Ser Leu Thr Asp Leu Glu Ile Trp Ser
                85                  90                  95

Asn Gln Asp Leu Ile Asn Val Gln Ser Ala Ala Ala Asp Thr Leu Lys
            100                 105                 110
```

```
Thr Phe Gly Glu Trp Arg Glu Arg Val Leu Leu Asn Arg Ile Ser His
            115                 120                 125

Asp Asn Ala Gln Leu Leu Thr Ala Ile Asp Leu Ala Asp Asn Thr Ile
        130                 135                 140

Gly Ile Ala Tyr Thr Gly Gly Met Cys Tyr Pro Lys Asn Ser Val Gly
145                 150                 155                 160

Ile Val Gln Asp His Ser Pro Lys Thr Leu Leu Ile Ala Val Thr Met
                165                 170                 175

Ala His Glu Leu Gly His Asn Leu Gly Met Lys His Asp Glu Asn His
            180                 185                 190

Cys His Cys Ser Ala Ser Phe Cys Ile Met Pro Pro Ser Leu Ser Glu
        195                 200                 205

Gly Pro Ser Tyr Glu Phe Ser Asp Cys Ser Lys Asp Tyr Tyr Glu Met
210                 215                 220

Phe Leu Thr Lys Arg Lys Pro Gln Cys Ile Leu Asn Lys Pro Trp Tyr
225                 230                 235                 240

His Gly Ile Arg Ser Leu Ile Arg Leu Leu Thr Lys Pro Glu Arg Lys
                245                 250                 255

Leu Ser Trp Leu Leu Pro Pro Leu Ser Asn Asn
            260                 265

<210> SEQ ID NO 4
<211> LENGTH: 8
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 4

His Asp Asn Ala Gln Leu Leu Thr
1               5

<210> SEQ ID NO 5
<211> LENGTH: 16
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 5

Ala Ile Asp Leu Ala Asp Asn Thr Ile Gly Ile Ala Tyr Thr Gly Gly
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 6

Gln Leu Leu Thr Ala Ile Asp Leu
1               5

<210> SEQ ID NO 7
<211> LENGTH: 8
<212> TYPE: PRT
<213> ORGANISM: Artificial Sequence
<220> FEATURE:
<223> OTHER INFORMATION: NH2-COOH terminal peptide sequence from the
``` sequence of SEQ ID NO: 2

<400> SEQUENCE: 7

Ala Asp Asn Thr Ile Gly Ile Ala
1               5

<210> SEQ ID NO 8
<211> LENGTH: 8
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 8

Ile Gly Ile Ala Tyr Thr Gly Gly
1               5

<210> SEQ ID NO 9
<211> LENGTH: 9
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 9

Asn Ala Gln Leu Leu Thr Ala Ile Asp
1               5

<210> SEQ ID NO 10
<211> LENGTH: 8
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 10

Tyr Thr Gly Gly Met Cys Tyr Pro
1               5

<210> SEQ ID NO 11
<211> LENGTH: 5
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 11

Leu Thr Ala Ile Asp
1               5

<210> SEQ ID NO 12
<211> LENGTH: 5
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 12

Ala Ile Asp Leu Ala
1               5

<210> SEQ ID NO 13

```
<211> LENGTH: 7
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 13

Leu Thr Ala Ile Asp Leu Ala
 1               5

<210> SEQ ID NO 14
<211> LENGTH: 3
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 14

Ala Ile Asp
 1

<210> SEQ ID NO 15
<211> LENGTH: 29
<212> TYPE: PRT
<213> ORGANISM: Artificial Sequence
<220> FEATURE:
<223> OTHER INFORMATION: NH2-COOH terminal peptide sequence from the
      sequence of SEQ ID NO: 2

<400> SEQUENCE: 15

Leu Asn Arg Ile Ser His Asp Asn Ala Gln Leu Leu Thr Ala Ile Asp
 1               5                  10                  15

Leu Ala Asp Asn Thr Ile Gly Ile Ala Tyr Thr Gly Gly
            20                  25

<210> SEQ ID NO 16
<211> LENGTH: 24
<212> TYPE: DNA
<213> ORGANISM: Artificial Sequence
<220> FEATURE:
<223> OTHER INFORMATION: degenerated oligonucleotide ("sense primer")

<400> SEQUENCE: 16
ttctcmsara aatacatyga actg                                          24

<210> SEQ ID NO 17
<211> LENGTH: 21
<212> TYPE: DNA
<213> ORGANISM: Artificial Sequence
<220> FEATURE:
<223> OTHER INFORMATION: degenerated oligonucleotide ("antisense
      primer")

<400> SEQUENCE: 17
wggyttrttc aggatrcatt g                                             21

<210> SEQ ID NO 18
<211> LENGTH: 31
<212> TYPE: DNA
<213> ORGANISM: Artificial Sequence
<220> FEATURE:
<223> OTHER INFORMATION: sense oligonucleotide for the SEQ ID NO: 2
      coding nucleotide sequence having the restriction site
      Xho-I at 5' end

<400> SEQUENCE: 18
```

-continued

```
ctcgagttct cccagaaata cattgaactg g                                    31
```

<210> SEQ ID NO 19
<211> LENGTH: 21
<212> TYPE: DNA
<213> ORGANISM: Artificial Sequence
<220> FEATURE:
<223> OTHER INFORMATION: sense oligonucleotide for the SEQ ID NO: 2
      coding nucleotide sequence having the restriction site
      Nco-I at 3' end

<400> SEQUENCE: 19

```
atcctgaaca aacctccatg g                                               21
```

<210> SEQ ID NO 20
<211> LENGTH: 20
<212> TYPE: DNA
<213> ORGANISM: Artificial Sequence
<220> FEATURE:
<223> OTHER INFORMATION: sense oligonucleotide for the T7 polymerase
      promoter coding nucleotide sequence

<400> SEQUENCE: 20

```
taatacgact cactataggg                                                 20
```

<210> SEQ ID NO 21
<211> LENGTH: 20
<212> TYPE: DNA
<213> ORGANISM: Artificial Sequence
<220> FEATURE:
<223> OTHER INFORMATION: antisense oligonucleotide for the SP6
      polymerase coding nucleotide sequence

<400> SEQUENCE: 21

```
ttctatagtg tcacctaaat                                                 20
```

<210> SEQ ID NO 22
<211> LENGTH: 14
<212> TYPE: PRT
<213> ORGANISM: Artificial Sequence
<220> FEATURE:
<223> OTHER INFORMATION: NH2-COOH terminal peptide sequence

<400> SEQUENCE: 22

Ser Asn Gln Asp Leu Ile Asn Val Gln Ser Arg Arg Arg Asp
 1               5                  10

<210> SEQ ID NO 23
<211> LENGTH: 414
<212> TYPE: PRT
<213> ORGANISM: Crotalus atrox

<400> SEQUENCE: 23

Met Ile Glu Val Val Leu Val Thr Ile Cys Leu Ala Val Phe Pro Tyr
 1               5                  10                  15

Gln Gly Ser Ser Ile Ile Leu Glu Ser Gly Asn Val Asn Asp Tyr Glu
                20                  25                  30

Val Val Tyr Pro Arg Lys Val Thr Ala Leu Pro Lys Gly Ala Val Gln
            35                  40                  45

Pro Lys Tyr Glu Asp Ala Met Gln Tyr Glu Leu Lys Val Asn Gly Glu
        50                  55                  60

Pro Val Val Leu His Leu Glu Lys Asn Lys Glu Leu Phe Ser Lys Asp
65                  70                  75                  80

```
Tyr Ser Glu Thr His Tyr Ser Pro Asp Gly Arg Lys Ile Thr Thr Asn
             85                  90                  95

Pro Ser Val Glu Asp His Cys Tyr Tyr Arg Gly Arg Ile Glu Asn Asp
            100                 105                 110

Ala Asp Ser Thr Ala Ser Ile Ser Ala Cys Asn Gly Leu Lys Gly His
            115                 120                 125

Phe Lys Leu Gln Gly Glu Leu Tyr Leu Ile Glu Pro Leu Glu Leu Ser
            130                 135                 140

Asp Ser Glu Ala His Ala Val Phe Lys Leu Glu Asn Val Glu Lys Glu
145                 150                 155                 160

Asp Glu Ala Pro Lys Met Cys Gly Val Thr Gln Asn Trp Glu Ser Tyr
                165                 170                 175

Glu Pro Ile Lys Lys Ala Ser Asp Leu Asn Leu Asn Pro Asp Gln Gln
            180                 185                 190

Asn Leu Pro Gln Arg Tyr Ile Glu Leu Val Val Val Ala Asp His Arg
            195                 200                 205

Val Phe Met Lys Tyr Asn Ser Asp Leu Asn Thr Ile Arg Thr Arg Val
            210                 215                 220

His Glu Ile Val Asn Phe Ile Asn Gly Phe Tyr Arg Ser Leu Asn Ile
225                 230                 235                 240

His Val Ser Leu Thr Asp Leu Glu Ile Trp Ser Asn Glu Asp Gln Ile
                245                 250                 255

Asn Ile Gln Ser Ala Ser Ser Asp Thr Leu Asn Ala Phe Ala Glu Trp
            260                 265                 270

Arg Glu Thr Asp Leu Leu Asn Arg Lys Ser His Asp Asn Ala Gln Leu
            275                 280                 285

Leu Thr Ala Ile Glu Leu Asp Glu Glu Thr Leu Gly Leu Ala Pro Leu
290                 295                 300

Gly Thr Met Cys Asp Pro Lys Leu Ser Ile Gly Ile Val Gln Asp His
305                 310                 315                 320

Ser Pro Ile Asn Leu Leu Met Gly Val Thr Met Ala His Glu Leu Gly
            325                 330                 335

His Asn Leu Gly Met Glu His Asp Gly Lys Asp Cys Leu Arg Gly Ala
            340                 345                 350

Ser Leu Cys Ile Met Arg Pro Gly Leu Thr Lys Gly Arg Ser Tyr Glu
            355                 360                 365

Phe Ser Ala Asp Ser Met His Tyr Tyr Glu Arg Phe Leu Lys Gln Tyr
            370                 375                 380

Lys Pro Gln Cys Ile Leu Asn Lys Pro Leu Arg Ile Asp Pro Val Ser
385                 390                 395                 400

Thr Pro Val Ser Gly Asn Glu Leu Leu Glu Ala Gly Glu Glu
                405                 410

<210> SEQ ID NO 24
<211> LENGTH: 202
<212> TYPE: PRT
<213> ORGANISM: Crotalus adamanteus

<400> SEQUENCE: 24

Glu Asn Leu Pro Gln Arg Tyr Ile Glu Leu Val Val Val Ala Asp Arg
 1               5                  10                  15

Arg Val Phe Met Lys Tyr Asn Ser Asp Leu Asn Ile Ile Arg Thr Arg
                20                  25                  30

Val His Glu Ile Val Asn Ile Ile Asn Lys Phe Tyr Arg Ser Leu Asn
            35                  40                  45
```

```
Ile Arg Val Ser Leu Thr Asp Leu Glu Ile Trp Ser Gly Gln Asp Phe
            50                  55                  60

Ile Thr Ile Gln Ser Ser Ser Asn Thr Leu Asn Ser Phe Gly Glu
 65              70                  75                  80

Trp Arg Glu Arg Val Leu Leu Ile Trp Lys Arg His Asp Asn Ala Gln
                    85                  90                  95

Leu Leu Thr Ala Ile Asn Phe Glu Gly Lys Ile Ile Gly Lys Ala Tyr
                100                 105                 110

Thr Ser Ser Met Cys Asn Pro Arg Ser Ser Val Gly Ile Val Lys Asp
            115                 120                 125

His Ser Pro Ile Asn Leu Leu Val Ala Val Thr Met Ala His Glu Leu
            130                 135                 140

Gly His Asn Leu Gly Met Glu His Asp Gly Lys Asp Cys Leu Arg Gly
145                 150                 155                 160

Ala Ser Leu Cys Ile Met Arg Pro Gly Leu Thr Pro Gly Arg Ser Tyr
                165                 170                 175

Glu Phe Ser Asp Asp Ser Met Gly Tyr Tyr Gln Lys Phe Leu Asn Gln
                180                 185                 190

Tyr Lys Pro Gln Cys Ile Leu Asn Lys Pro
            195                 200

<210> SEQ ID NO 25
<211> LENGTH: 407
<212> TYPE: PRT
<213> ORGANISM: Agkistrodon contortrix laticinctus

<400> SEQUENCE: 25

Met Ile Gln Val Leu Leu Val Thr Leu Cys Leu Ala Ala Phe Pro Tyr
 1                5                  10                  15

Gln Gly Ser Ser Ile Ile Leu Glu Ser Gly Asn Val Asn Asp Tyr Glu
                20                  25                  30

Val Val Tyr Pro Arg Lys Val Thr Pro Val Pro Lys Gly Ala Val Gln
             35                  40                  45

Pro Lys Tyr Glu Asp Ala Met Gln Tyr Glu Leu Lys Val Asn Gly Glu
 50                  55                  60

Pro Val Val Leu His Leu Glu Arg Asn Lys Gly Leu Phe Ser Lys Asp
 65                  70                  75                  80

Tyr Ser Glu Thr His Tyr Ser Pro Asp Gly Arg Lys Ile Thr Thr Tyr
                 85                  90                  95

Pro Pro Val Glu Asp His Cys Tyr Tyr His Gly Arg Ile Gln Asn Asp
            100                 105                 110

Ala Asp Ser Ile Ala Ser Ile Ser Ala Cys Asn Gly Leu Lys Gly His
            115                 120                 125

Phe Lys Leu Gln Gly Glu Met Tyr Leu Ile Glu Pro Leu Glu Leu Ser
130                 135                 140

Asp Ser Glu Ala His Ala Val Phe Lys Tyr Glu Asn Val Glu Lys Glu
145                 150                 155                 160

Asp Glu Ala Pro Lys Ile Cys Gly Val Thr Gln Asn Trp Glu Ser Tyr
                165                 170                 175

Glu Pro Ile Lys Lys Ala Ser Gln Leu Asn Leu Asn Tyr Gln Tyr Gln
                180                 185                 190

Arg Tyr Val Glu Leu Val Thr Val Val Asp His Gly Met Tyr Thr Lys
                195                 200                 205

Tyr Asn Gly Asp Ser Asp Lys Ile Arg Gln Trp Val His Gln Met Val
```

```
                210              215              220
Asn Thr Met Lys Glu Ser Tyr Arg Tyr Met Tyr Ile Asp Ile Ser Leu
225              230              235              240

Ala Gly Val Glu Ile Trp Ser Asn Lys Asp Leu Ile Asp Val Gln Pro
                245              250              255

Ala Ala Arg His Thr Leu Asp Ser Phe Gly Glu Trp Arg Glu Arg Asp
                260              265              270

Leu Leu His Arg Ile Ser His Asp Asn Ala Gln Leu Leu Thr Ser Thr
                275              280              285

Asp Phe Asp Gly Pro Thr Ile Gly Leu Ala Tyr Val Gly Thr Met Cys
                290              295              300

Asp Pro Lys Leu Ser Thr Gly Val Val Glu Asp His Ser Lys Ile Asn
305              310              315              320

Phe Leu Val Ala Val Thr Met Ala His Glu Met Gly His Asn Leu Gly
                325              330              335

Met Arg His Asp Thr Gly Ser Cys Ser Cys Gly Gly Tyr Ser Cys Ile
                340              345              350

Met Ser Pro Val Ile Ser Asp Asp Ser Pro Lys Tyr Phe Ser Asn Cys
                355              360              365

Ser Tyr Ile Gln Cys Trp Asp Phe Ile Met Lys Glu Asn Pro Gln Cys
                370              375              380

Ile Leu Asn Lys Pro Leu Arg Thr Asp Thr Val Ser Thr Pro Val Ser
385              390              395              400

Gly Asp Glu Leu Leu Glu Ala
                405

<210> SEQ ID NO 26
<211> LENGTH: 200
<212> TYPE: PRT
<213> ORGANISM: Lachesis muta muta

<400> SEQUENCE: 26

Phe Ser Gln Lys Tyr Ile Glu Leu Val Val Ala Asp His Gly Met
1               5                10               15

Phe Thr Lys Tyr Asn Gly Asn Leu Asn Thr Ile Arg Thr Arg Val His
                20               25               30

Glu Ile Val Asn Thr Leu Asn Gly Phe Tyr Arg Ser Leu Asn Ile Leu
                35               40               45

Ile Ser Leu Thr Asp Leu Glu Ile Trp Ser Asn Gln Asp Leu Ile Asn
                50               55               60

Val Gln Ser Ala Ala Asn Asp Thr Leu Lys Thr Phe Gly Glu Trp Arg
65               70               75               80

Glu Arg Val Leu Leu Asn Arg Ile Ser His Asp Asn Ala Gln Leu Leu
                85               90               95

Thr Ala Ile Asp Leu Ala Asp Asn Thr Ile Gly Ile Ala Tyr Thr Gly
                100              105              110

Gly Met Cys Tyr Pro Lys Asn Ser Val Gly Ile Val Gln Asp His Ser
                115              120              125

Pro Lys Thr Leu Leu Ile Ala Val Thr Met Ala His Glu Leu Gly His
                130              135              140

Asn Leu Gly Met Lys His Asp Glu Asn His Cys His Cys Ser Ala Ser
145              150              155              160

Phe Cys Ile Met Pro Pro Ser Ile Ser Glu Gly Pro Ser Tyr Glu Phe
                165              170              175
```

Ser Asp Cys Ser Lys Asp Tyr Gln Met Phe Leu Thr Lys Arg Lys
              180                 185                 190

Pro Gln Cys Ile Leu Asn Lys Pro
        195                 200

<210> SEQ ID NO 27
<211> LENGTH: 203
<212> TYPE: PRT
<213> ORGANISM: Agkistrodon contortrix

<400> SEQUENCE: 27

Glu Gln Arg Phe Pro Gln Arg Tyr Val Gln Leu Val Ile Val Ala Asp
1               5                   10                  15

His Arg Met Asn Thr Lys Tyr Asn Gly Asp Ser Asp Lys Ile Arg Gln
            20                  25                  30

Trp Val His Gln Ile Val Asn Thr Ile Asn Glu Ile Tyr Arg Pro Leu
        35                  40                  45

Asn Ile Gln Phe Thr Leu Val Gly Leu Glu Ile Trp Ser Asn Gln Asp
    50                  55                  60

Leu Ile Thr Val Thr Ser Val Ser His Asp Thr Leu Ala Ser Phe Gly
65                  70                  75                  80

Asn Trp Arg Glu Thr Asp Leu Leu Arg Arg Gln Arg His Asp Asn Ala
                85                  90                  95

Gln Leu Leu Thr Ala Ile Asp Phe Asp Gly Asp Thr Val Gly Leu Ala
            100                 105                 110

Tyr Val Gly Gly Met Cys Gln Leu Lys His Ser Thr Gly Val Ile Gln
        115                 120                 125

Asp His Ser Ala Ile Asn Leu Leu Val Ala Leu Thr Met Ala His Glu
    130                 135                 140

Leu Gly His Asn Leu Gly Met Asn His Asp Gly Asn Gln Cys His Cys
145                 150                 155                 160

Gly Ala Asn Ser Cys Val Met Ala Ala Met Leu Ser Asp Gln Pro Ser
                165                 170                 175

Lys Leu Phe Ser Asp Cys Ser Lys Lys Asp Tyr Gln Thr Phe Leu Thr
            180                 185                 190

Val Asn Asn Pro Gln Cys Ile Leu Asn Lys Pro
        195                 200

<210> SEQ ID NO 28
<211> LENGTH: 478
<212> TYPE: PRT
<213> ORGANISM: Macrovipera lebetina

<400> SEQUENCE: 28

Met Ile Gln Val Leu Leu Val Thr Ile Cys Leu Ala Val Phe Pro Tyr
1               5                   10                  15

Gln Gly Ser Ser Lys Thr Leu Lys Ser Gly Asn Val Asn Asp Tyr Glu
            20                  25                  30

Val Val Asn Pro Gln Ala Val Thr Gly Leu Pro Lys Gly Ala Val Lys
        35                  40                  45

Gln Pro Glu Lys Lys Tyr Glu Asp Thr Met Gln Tyr Glu Phe Glu Val
    50                  55                  60

Asn Gly Glu Pro Val Val Leu His Leu Glu Lys Asn Arg Gly Leu Phe
65                  70                  75                  80

Ser Lys Asp Tyr Ser Glu Thr His Tyr Ser Pro Asp Gly Arg Glu Ile
                85                  90                  95

```
Thr Thr Asn Pro Ala Val Glu Asp His Cys Tyr Tyr His Gly Arg Ile
            100                 105                 110
Gln Asn Asp Ala Asp Ser Thr Ala Ser Ile Ser Ala Cys Asn Gly Leu
        115                 120                 125
Lys Gly Tyr Phe Thr Leu Arg Gly Glu Thr Tyr Leu Ile Glu Pro Leu
    130                 135                 140
Lys Leu Pro Asp Ser Glu Ala His Ala Val Tyr Lys Tyr Glu Asn Ile
145                 150                 155                 160
Glu Lys Glu Asp Glu Ala Pro Lys Met Cys Gly Val Thr Gln Thr Asn
                165                 170                 175
Trp Ala Ser Asp Glu Pro Ile Lys Lys Ala Ser Gln Leu Asn Leu Thr
            180                 185                 190
Pro Glu Gln Gln Arg Phe Glu Pro Arg Tyr Ile Glu Leu Val Ile Val
        195                 200                 205
Ala Asp His Ala Met Val Thr Lys Tyr Asn Gly Asp Leu Ala Ala Ile
    210                 215                 220
Thr Thr Trp Val His Gln Leu Val Asn Ile Asn Gly Phe Tyr Arg
225                 230                 235                 240
Asp Leu Asn Val His Ile Thr Leu Ser Ala Val Glu Val Trp Thr Asn
                245                 250                 255
Gly Asp Leu Ile Asn Val Gln Pro Ala Ala Ser Val Thr Leu Asn Leu
            260                 265                 270
Phe Gly Glu Trp Arg Glu Arg Asp Leu Leu Asn Arg Met His Asp
        275                 280                 285
His Ala Gln Leu Leu Thr Gly Ile Asp Leu Asp Asp Asn Ile Ile Gly
    290                 295                 300
Leu Ala Tyr Asp Asp Ser Met Cys Asp Pro Arg Tyr Ser Val Gly Ile
305                 310                 315                 320
Val Gln Asp His Ser Ala Ile Ile Arg Leu Val Ala Val Thr Met Ala
                325                 330                 335
His Glu Leu Gly His Asn Leu Gly Met Asn His Asp Gly Asp Gln Cys
            340                 345                 350
Asn Cys Gly Ala Asn Gly Cys Val Met Ser Val Val Leu Ile Glu Gln
        355                 360                 365
Arg Ser Tyr Gln Phe Ser Asp Cys Ser Lys Asn Lys Tyr Gln Thr Tyr
    370                 375                 380
Leu Thr Asn Arg Asn Pro Gln Cys Ile Leu Asn Gln Pro Leu Arg Thr
385                 390                 395                 400
Asp Thr Val Ser Thr Pro Val Ser Gly Asn Glu Leu Leu Gln Asn Ser
                405                 410                 415
Gly Asn Pro Cys Cys Asp Pro Val Thr Cys Gln Pro Arg Arg Gly Glu
            420                 425                 430
His Cys Val Ser Gly Lys Cys Cys Arg Asn Cys Lys Phe Leu Arg Ala
        435                 440                 445
Gly Thr Val Cys Lys Arg Ala Val Gly Asp Asp Met Asp Asp Tyr Cys
    450                 455                 460
Thr Gly Ile Ser Ser Asp Cys Pro Arg Asn Pro Tyr Lys Asp
465                 470                 475

<210> SEQ ID NO 29
<211> LENGTH: 614
<212> TYPE: PRT
<213> ORGANISM: Protobothrops flavoviridis

<400> SEQUENCE: 29
```

```
Met Ile Gln Val Leu Leu Val Thr Ile Cys Leu Ala Val Phe Pro Tyr
  1               5                  10                 15

Gln Gly Ser Ser Ile Ile Leu Glu Ser Gly Asn Val Asn Asp Tyr Glu
                 20                  25                 30

Val Met Tyr Pro Gln Lys Val Ala Ala Leu Pro Lys Gly Ala Val Gln
             35                  40                  45

Gln Lys Tyr Glu Asp Thr Met Gln Tyr Glu Phe Lys Val Asn Gly Glu
 50                  55                  60

Pro Val Val Leu His Leu Glu Lys Asn Lys Gly Leu Phe Ser Glu Asp
 65                  70                  75                  80

Tyr Ser Glu Thr His Tyr Ser Pro Asp Gly Arg Glu Ile Thr Thr Asn
                 85                  90                  95

Pro Pro Val Glu Asp His Cys Tyr Tyr His Gly Arg Ile Gln Asn Asp
            100                 105                 110

Ala Asp Ser Thr Ala Ser Ile Ser Ala Cys Asn Gly Leu Lys Gly His
        115                 120                 125

Phe Lys Leu Gln Gly Glu Met Tyr Leu Ile Glu Pro Leu Lys Phe Ser
    130                 135                 140

Asp Ser Glu Ala His Ala Val Tyr Lys Tyr Glu Asn Val Glu Lys Glu
145                 150                 155                 160

Glu Glu Ala Pro Lys Met Cys Gly Val Thr Gln Thr Asn Trp Glu Ser
                165                 170                 175

Asp Glu Pro Ile Lys Lys Ala Ser Lys Leu Val Val Thr Ala Glu Gln
            180                 185                 190

Gln Arg Phe Pro Arg Arg Tyr Ile Lys Leu Ala Ile Val Val Asp His
        195                 200                 205

Gly Ile Val Thr Lys His His Gly Asn Leu Lys Lys Ile Arg Lys Trp
    210                 215                 220

Ile Tyr Gln Leu Val Asn Thr Ile Asn Asn Ile Tyr Arg Ser Leu Asn
225                 230                 235                 240

Ile Leu Val Ala Leu Val Tyr Leu Glu Ile Trp Ser Lys Gln Asn Lys
                245                 250                 255

Ile Thr Val Gln Ser Ala Ser Asn Val Thr Leu Asp Leu Phe Gly Asp
            260                 265                 270

Trp Arg Glu Ser Val Leu Leu Lys Gln Arg Ser His Asp Cys Ala Gln
        275                 280                 285

Leu Leu Thr Thr Ile Asp Phe Asp Gly Pro Thr Ile Gly Lys Ala Tyr
    290                 295                 300

Thr Ala Ser Met Cys Asp Pro Lys Arg Ser Val Gly Ile Val Gln Asp
305                 310                 315                 320

Tyr Ser Pro Ile Asn Leu Val Val Ala Val Ile Met Thr His Glu Met
                325                 330                 335

Gly His Asn Leu Gly Ile Pro His Asp Gly Asn Ser Cys Thr Cys Gly
            340                 345                 350

Gly Phe Pro Cys Ile Met Ser Pro Met Ile Ser Asp Pro Pro Ser Glu
        355                 360                 365

Leu Phe Ser Asn Cys Ser Lys Ala Tyr Tyr Gln Thr Phe Leu Thr Asp
    370                 375                 380

His Lys Pro Gln Cys Ile Leu Asn Ala Pro Ser Lys Thr Asp Ile Val
385                 390                 395                 400

Ser Pro Pro Val Cys Gly Asn Glu Leu Leu Glu Ala Gly Glu Glu Cys
                405                 410                 415
```

```
Asp Cys Gly Ser Pro Glu Asn Cys Gln Tyr Gln Cys Cys Asp Ala Ala
            420                 425                 430

Ser Cys Lys Leu His Ser Trp Val Lys Cys Glu Ser Gly Glu Cys Cys
            435                 440                 445

Asp Gln Cys Arg Phe Arg Thr Ala Gly Thr Glu Cys Arg Ala Ala Glu
            450                 455                 460

Ser Glu Cys Asp Ile Pro Glu Ser Cys Thr Gly Gln Ser Ala Asp Cys
465                 470                 475                 480

Pro Thr Asp Arg Phe His Arg Asn Gly Gln Pro Cys Leu Tyr Asn His
            485                 490                 495

Gly Tyr Cys Tyr Asn Gly Lys Cys Pro Ile Met Phe Tyr Gln Cys Tyr
            500                 505                 510

Phe Leu Phe Gly Ser Asn Ala Thr Val Ala Glu Asp Cys Phe Asn
            515                 520                 525

Asn Asn Lys Lys Gly Asp Lys Tyr Phe Tyr Cys Arg Lys Glu Asn Glu
            530                 535                 540

Lys Tyr Ile Pro Cys Ala Gln Glu Asp Val Lys Cys Gly Arg Leu Phe
545                 550                 555                 560

Cys Asp Asn Lys Lys Tyr Pro Cys His Tyr Asn Tyr Ser Glu Asp Leu
            565                 570                 575

Asp Phe Gly Met Val Asp His Gly Thr Lys Cys Ala Asp Gly Lys Val
            580                 585                 590

Cys Ser Asn Arg Gln Cys Val Asp Val Asn Glu Ala Tyr Lys Ser Thr
            595                 600                 605

Thr Val Phe Ser Leu Ile
            610

<210> SEQ ID NO 30
<211> LENGTH: 201
<212> TYPE: PRT
<213> ORGANISM: Protobothrops flavoviridis

<400> SEQUENCE: 30

Gln Arg Phe Pro Gln Arg Tyr Ile Glu Leu Ala Ile Val Val Asp His
1               5                   10                  15

Gly Met Tyr Lys Lys Tyr Asn Gln Asn Ser Asp Lys Ile Lys Val Arg
            20                  25                  30

Val His Gln Met Val Asn His Ile Asn Glu Met Tyr Arg Pro Leu Asn
        35                  40                  45

Ile Ala Ile Ser Leu Asn Arg Leu Gln Ile Trp Ser Lys Lys Asp Leu
    50                  55                  60

Ile Thr Val Lys Ser Ala Ser Asn Val Thr Leu Glu Ser Phe Gly Asn
65                  70                  75                  80

Trp Arg Glu Thr Val Leu Leu Lys Gln Gln Asn Asn Asp Cys Ala His
            85                  90                  95

Leu Leu Thr Ala Thr Asn Leu Asn Asp Asn Thr Ile Gly Leu Ala Tyr
            100                 105                 110

Lys Lys Gly Met Cys Asn Pro Lys Leu Ser Val Gly Leu Val Gln Asp
        115                 120                 125

Tyr Ser Pro Asn Val Phe Met Val Ala Val Thr Met Thr His Glu Leu
    130                 135                 140

Gly His Asn Leu Gly Met Glu His Asp Asp Lys Asp Lys Cys Lys Cys
145                 150                 155                 160

Glu Ala Cys Ile Met Ser Asp Val Ile Ser Asp Lys Pro Ser Lys Leu
            165                 170                 175
```

Phe Ser Asp Cys Ser Lys Asn Asp Tyr Gln Thr Phe Leu Thr Lys Tyr
                180                 185                 190

Asn Pro Gln Cys Ile Leu Asn Ala Pro
            195                 200

<210> SEQ ID NO 31
<211> LENGTH: 480
<212> TYPE: PRT
<213> ORGANISM: Trimeresurus gramineus

<400> SEQUENCE: 31

Met Ile Gln Val Leu Leu Ile Thr Ile Cys Leu Ala Val Phe Pro Tyr
 1               5                  10                  15

Gln Gly Ser Ser Ile Ile Leu Glu Ser Gly Asn Leu Asn Asp Tyr Glu
                20                  25                  30

Val Val Tyr Pro Glu Lys Val Thr Ala Leu Pro Lys Gly Ala Val Gln
             35                  40                  45

Gln Lys Tyr Glu Asp Ala Met Gln Tyr Glu Phe Lys Val Asn Gly Glu
     50                  55                  60

Pro Val Val Leu His Leu Glu Lys Asn Lys Gly Leu Phe Ser Glu Asp
65                  70                  75                  80

Tyr Ser Glu Ile His Tyr Ser Pro Asp Gly Arg Glu Ile Thr Ala Tyr
                85                  90                  95

Pro Ser Val Glu Asp His Cys Tyr Tyr His Gly Arg Ile Glu Asn Asp
            100                 105                 110

Ala Asp Ser Thr Ala Ser Ile Ser Ala Cys Asp Gly Leu Lys Gly His
        115                 120                 125

Phe Lys Leu Gln Gly Glu Met Tyr Leu Ile Glu Pro Leu Glu Leu Ser
    130                 135                 140

Asp Ser Glu Ala His Ala Val Phe Lys Tyr Glu Asn Val Glu Lys Glu
145                 150                 155                 160

Asp Glu Pro Pro Lys Met Cys Gly Val Thr Gln Asn Trp Glu Ser Tyr
                165                 170                 175

Glu Ser Thr Lys Lys Ala Ser Gln Leu Asn Val Thr Pro Glu Gln Gln
            180                 185                 190

Arg Phe Pro Gln Arg Tyr Ile Lys Leu Gly Ile Phe Val Asp His Gly
        195                 200                 205

Met Tyr Thr Lys Tyr Ser Gly Asn Ser Glu Arg Ile Thr Lys Arg Val
    210                 215                 220

His Gln Met Ile Asn Asn Ile Asn Met Met Cys Arg Ala Leu Asn Ile
225                 230                 235                 240

Val Thr Thr Leu Ser Val Leu Glu Ile Trp Ser Glu Lys Asp Leu Ile
                245                 250                 255

Thr Val Gln Ala Ser Ala Pro Thr Thr Leu Thr Leu Phe Gly Ala Trp
            260                 265                 270

Arg Glu Thr Val Leu Leu Asn Arg Thr Ser His Asp His Ala Gln Leu
        275                 280                 285

Leu Thr Ala Thr Ile Phe Asn Gly Asn Val Ile Gly Arg Ala Pro Val
    290                 295                 300

Gly Gly Met Cys Asp Pro Lys Arg Ser Val Ala Ile Val Arg Asp His
305                 310                 315                 320

Asn Ala Ile Val Phe Val Val Ala Val Thr Met Thr His Glu Met Gly
                325                 330                 335

His Asn Leu Gly Met His His Asp Glu Asp Lys Cys Asn Cys Asn Thr

-continued

```
              340                 345                 350
Cys Ile Met Ser Lys Val Leu Ser Arg Gln Pro Ser Lys Tyr Phe Ser
            355                 360                 365

Glu Cys Ser Lys Asp Tyr Tyr Gln Thr Phe Leu Thr Asn His Asn Pro
        370                 375                 380

Gln Cys Ile Leu Asn Ala Pro Leu Arg Thr Asp Thr Val Ser Thr Pro
385                 390                 395                 400

Val Ser Gly Asn Glu Leu Leu Glu Ala Gly Glu Asp Cys Asp Cys Gly
                405                 410                 415

Ser Pro Ala Asn Pro Cys Cys Asp Ala Ala Thr Cys Lys Leu Ile Pro
                420                 425                 430

Gly Ala Gln Cys Gly Glu Gly Leu Cys Cys Asp Gln Cys Ser Phe Ile
            435                 440                 445

Glu Glu Gly Thr Val Cys Arg Ile Ala Arg Gly Asp Asp Leu Asp Asp
        450                 455                 460

Tyr Cys Asn Gly Arg Ser Ala Gly Cys Pro Arg Asn Pro Phe His Ala
465                 470                 475                 480
```